(12) United States Patent
Minagawa

(10) Patent No.: US 10,280,274 B2
(45) Date of Patent: May 7, 2019

(54) METHOD FOR MODIFYING SURFACE AND SURFACE MODIFIED ELASTIC BODY

(71) Applicant: SUMITOMO RUBBER INDUSTRIES, LTD., Kobe-shi, Hyogo (JP)

(72) Inventor: Yasuhisa Minagawa, Kobe (JP)

(73) Assignee: SUMITOMO RUBBER INDUSTRIES, LTD., Kobe-shi, Hyogo (JP)

( * ) Notice: Subject to any disclaimer, the term of this patent is extended or adjusted under 35 U.S.C. 154(b) by 0 days.

(21) Appl. No.: 15/107,039

(22) PCT Filed: Dec. 8, 2014

(86) PCT No.: PCT/JP2014/082367
§ 371 (c)(1),
(2) Date: Jun. 21, 2016

(87) PCT Pub. No.: WO2015/102072
PCT Pub. Date: Jul. 9, 2015

(65) Prior Publication Data
US 2017/0037212 A1     Feb. 9, 2017

(30) Foreign Application Priority Data
Jan. 6, 2014   (JP) .................. 2014-000515

(51) Int. Cl.
*C08J 7/18*     (2006.01)
*A61M 5/315*    (2006.01)
(Continued)

(52) U.S. Cl.
CPC ............... *C08J 7/18* (2013.01); *A61M 5/315* (2013.01); *A61M 5/3129* (2013.01);
(Continued)

(58) Field of Classification Search
CPC ...... C08J 7/18; C08J 2315/02; C08J 2319/00; C08J 2323/28; B60C 1/0016;
(Continued)

(56) References Cited

U.S. PATENT DOCUMENTS 3,418,066 A   12/1968  Caldwell et al.
5,100,689 A    3/1992  Goldberg et al.
(Continued)

FOREIGN PATENT DOCUMENTS

CN   101372538 A    2/2009
CN   101565489 A   10/2009
(Continued)

OTHER PUBLICATIONS

International Search Report for PCT/JP2014/082367 dated Mar. 3, 2015.
(Continued)

*Primary Examiner* — Sanza L. McClendon
(74) *Attorney, Agent, or Firm* — Birch, Stewart, Kolasch & Birch LLP

(57) ABSTRACT

The present invention provides a method for surface-modifying a rubber vulcanizate or a thermoplastic elastomer, which can cost-effectively provide a variety of functions, such as remarkable sliding properties or biocompatibility, according to the application. The present invention relates to a method for surface-modifying a rubber vulcanizate or a thermoplastic elastomer as a modification target, the method including: step 1 of forming polymerization initiation points A on a surface of the modification target; step 2 of radically polymerizing a non-functional monomer starting from the polymerization initiation points A to grow non-functional polymer chains; step 3 of washing the modification target on which the non-functional polymer chains are grown; step 4 of forming polymerization initiation points B on a surface of
(Continued)

the non-functional polymer chains; and step 5 of radically polymerizing a fluorine-containing functional monomer starting from the polymerization initiation points B to grow fluorine-containing functional polymer chains.

23 Claims, 4 Drawing Sheets

(51) Int. Cl.
    *B60C 11/00*    (2006.01)
    *B60C 1/00*    (2006.01)
    *B60C 11/13*    (2006.01)
    *A61M 5/31*    (2006.01)

(52) U.S. Cl.
    CPC .......... *B60C 1/0016* (2013.01); *B60C 1/0025* (2013.01); *B60C 11/00* (2013.01); *B60C 11/1346* (2013.01); *A61M 2005/3131* (2013.01); *C08J 2315/02* (2013.01); *C08J 2319/00* (2013.01); *C08J 2323/28* (2013.01)

(58) Field of Classification Search
    CPC ... B60C 1/0025; B60C 11/00; B60C 11/1346; A61M 5/3129; A61M 5/315; A61M 2005/3131
    See application file for complete search history.

(56) References Cited

U.S. PATENT DOCUMENTS

| | | | |
|---|---|---|---|
| 5,154,727 | A | 10/1992 | Dyer |
| 5,340,879 | A | 8/1994 | Audenaert et al. |
| 5,453,467 | A | 9/1995 | Bamford et al. |
| 5,637,460 | A | 6/1997 | Swan |
| 5,688,252 | A | 11/1997 | Matsuda et al. |
| 5,855,623 | A | 1/1999 | English et al. |
| 5,858,545 | A | 1/1999 | Everaerts et al. |
| 5,885,566 | A | 3/1999 | Goldberg |
| 5,889,073 | A | 3/1999 | Zhang et al. |
| 5,967,714 | A | 10/1999 | Ottersbach et al. |
| 6,001,894 | A | 12/1999 | Ottersbach et al. |
| 6,188,075 | B1 | 2/2001 | Takayama et al. |
| 6,203,856 | B1 | 3/2001 | Ottersbach et al. |
| 6,228,172 | B1 | 5/2001 | Taylor et al. |
| 6,358,557 | B1 | 3/2002 | Wang et al. |
| 6,808,738 | B2 | 10/2004 | Ditizio et al. |
| 7,348,055 | B2 | 3/2008 | Chappa et al. |
| 8,299,139 | B1 | 10/2012 | Taranekar et al. |
| 8,323,750 | B2 | 12/2012 | Yang et al. |
| 8,840,927 | B2 | 9/2014 | Ditizio et al. |
| 9,339,845 | B2 | 5/2016 | Minagawa |
| 9,469,736 | B2 | 10/2016 | Minagawa |
| 9,758,605 | B2 * | 12/2017 | Minagawa |
| 9,982,105 | B2 | 5/2018 | Minagawa |
| 2002/0161065 | A1 | 10/2002 | Ditizio et al. |
| 2004/0086568 | A1 | 5/2004 | Ditizio et al. |
| 2004/0106732 | A1 | 6/2004 | Tsuji et al. |
| 2005/0137355 | A1 | 6/2005 | Buckanin et al. |
| 2005/0168685 | A1 | 8/2005 | Katagiri et al. |
| 2006/0155057 | A1 | 7/2006 | Hermeling et al. |
| 2007/0003592 | A1 | 1/2007 | Hissink |
| 2007/0116971 | A1 | 5/2007 | Yoshikawa et al. |
| 2008/0016644 | A1 | 1/2008 | Mizote et al. |
| 2008/0103287 | A1 | 5/2008 | Chino et al. |
| 2008/0312377 | A1 | 12/2008 | Schmidt et al. |
| 2009/0169715 | A1 | 7/2009 | Dias et al. |
| 2009/0239089 | A1 | 9/2009 | Agata et al. |
| 2009/0257022 | A1 | 10/2009 | Abe et al. |
| 2010/0053547 | A1 | 3/2010 | Baude et al. |
| 2010/0255336 | A1 | 10/2010 | Zabinski |
| 2011/0124766 | A1 | 5/2011 | Yang et al. |
| 2011/0160357 | A1 | 6/2011 | Gerster et al. |
| 2011/0274940 | A1 | 11/2011 | Kyomoto et al. |
| 2012/0021151 | A1 | 1/2012 | Tatarka et al. |
| 2012/0100369 | A1 | 4/2012 | Hanazawa et al. |
| 2013/0158488 | A1 | 6/2013 | Weaver et al. |
| 2013/0158518 | A1 | 6/2013 | Li et al. |
| 2013/0203883 | A1 | 8/2013 | Minagawa |
| 2013/0274367 | A1 | 10/2013 | Minagawa et al. |
| 2013/0310772 | A1 | 11/2013 | Minagawa |
| 2014/0039084 | A1 | 2/2014 | Minagawa |
| 2014/0128493 | A1 | 5/2014 | Minagawa |
| 2014/0322468 | A1 | 10/2014 | Minagawa |
| 2015/0203612 | A1 | 7/2015 | Minagawa |
| 2016/0122488 | A1 | 5/2016 | Minagawa |

FOREIGN PATENT DOCUMENTS

| | | |
|---|---|---|
| CN | 102382291 A | 3/2012 |
| CN | 202427397 U | 9/2012 |
| CN | 103242553 A | 8/2013 |
| CN | 104119552 A | 10/2014 |
| EP | 0 872 512 A2 | 10/1998 |
| EP | 2 623 335 A2 | 8/2013 |
| EP | 2 664 627 A1 | 11/2013 |
| EP | 2 796 155 A1 | 10/2014 |
| EP | 2 894 191 A1 | 7/2015 |
| GB | 1120803 A | 7/1968 |
| GB | 1120804 A | 7/1968 |
| JP | 60-221410 A | 11/1985 |
| JP | 61-209667 A | 9/1986 |
| JP | 62-87163 A | 4/1987 |
| JP | 63-92658 A | 4/1988 |
| JP | 5-43634 A | 2/1993 |
| JP | 5-76590 A | 3/1993 |
| JP | 5-179055 A | 7/1993 |
| JP | 6-25450 A | 2/1994 |
| JP | 6-510322 A | 11/1994 |
| JP | 7-100744 B2 | 11/1995 |
| JP | 8-1793 A | 1/1996 |
| JP | 9-31361 A | 2/1997 |
| JP | 9-67457 A | 3/1997 |
| JP | 9-108359 A | 4/1997 |
| JP | 9-313594 A | 12/1997 |
| JP | 10-90500 A | 4/1998 |
| JP | 10-251350 A | 9/1998 |
| JP | 10-298320 A | 11/1998 |
| JP | 11-192305 A | 7/1999 |
| JP | 2000-273229 A | 10/2000 |
| JP | 2001-31871 A | 2/2001 |
| JP | 2001-46956 A | 2/2001 |
| JP | 2001-95621 A | 4/2001 |
| JP | 2002-145971 A | 5/2002 |
| JP | 2002-544346 A | 12/2002 |
| JP | 2003-2903 A | 1/2003 |
| JP | 2003-510378 A | 3/2003 |
| JP | 2004-528418 A | 9/2004 |
| JP | 2004-298220 A | 10/2004 |
| JP | 2005-3817 A | 1/2005 |
| JP | 2005-516736 A | 6/2005 |
| JP | 2005-208290 A | 8/2005 |
| JP | 2005-213516 A | 8/2005 |
| JP | 2005-523981 A | 8/2005 |
| JP | 2005-253538 A | 9/2005 |
| JP | 2007-77286 A | 3/2007 |
| JP | 2007-119563 A | 5/2007 |
| JP | 2007-145884 A | 6/2007 |
| JP | 2007-514861 A | 6/2007 |
| JP | 2007-202965 A | 8/2007 |
| JP | 2008-73883 A | 4/2008 |
| JP | 2009-30074 A | 2/2009 |
| JP | 2009-518479 A | 5/2009 |
| JP | 2009-138169 A | 6/2009 |
| JP | 2009-226718 A | 10/2009 |
| JP | 2009-227842 A | 10/2009 |
| JP | 2010-23710 A | 2/2010 |
| JP | 2010-508541 A | 3/2010 |
| JP | 2010-142537 A | 7/2010 |
| JP | 2010-142573 A | 7/2010 |
| JP | 2010-150349 A | 7/2010 |
| JP | 4523532 B2 | 8/2010 |
| JP | 2010-216964 A | 9/2010 |

(56) References Cited

FOREIGN PATENT DOCUMENTS

| | | |
|---|---|---|
| JP | 2010-229180 A | 10/2010 |
| JP | 2011-42755 A | 3/2011 |
| JP | 2011-67362 A | 4/2011 |
| JP | 2011-188908 A | 9/2011 |
| JP | 2011-189562 A | 9/2011 |
| JP | 2011-208133 A | 10/2011 |
| JP | 2011-219520 A | 11/2011 |
| JP | 2011-241190 A | 12/2011 |
| JP | 2012-105579 A | 6/2012 |
| JP | 2012-162646 A | 8/2012 |
| JP | 2013-159629 A | 8/2013 |
| JP | 2013-159667 A | 8/2013 |
| JP | 2013-208777 A | 10/2013 |
| JP | 2013-237801 A | 11/2013 |
| JP | 2013-237802 A | 11/2013 |
| JP | 2014-31429 A | 2/2014 |
| JP | 2014-31430 A | 2/2014 |
| JP | 2014-108153 A | 6/2014 |
| WO | WO 93/05081 A1 | 3/1993 |
| WO | WO 03/068289 A1 | 8/2003 |
| WO | WO 03/093357 A1 | 11/2003 |
| WO | WO 2007/065721 A2 | 6/2007 |
| WO | WO 2007/072613 A1 | 6/2007 |
| WO | WO 2008/053712 A1 | 5/2008 |
| WO | WO 2010/058848 A1 | 5/2010 |
| WO | WO 2010/131652 A1 | 11/2010 |
| WO | WO 2011/038483 A1 | 4/2011 |
| WO | WO 2012/091169 A1 | 7/2012 |
| WO | WO 2012/165525 A1 | 12/2012 |
| WO | WO 2014/203668 A1 | 12/2014 |

OTHER PUBLICATIONS

Written Opinion of the International Searching Authority for PCT/JP2014/082367 (PCT/ISA/237) dated Mar. 3, 2015.
Allmér et al., "Surface Modification of Polymers. I. Vapour Phase Photografting with Acrylic Acid," Journal of Polymer Science: Part A: Polymer Chemistry, vol. 26, 1988, pp. 2099-2111.
International Search Report issued in PCT/JP2013/074219 dated Dec. 3, 2013.
International Search Report, dated Jul. 24, 2012, for International Application No. PCT/JP2012/064030.
U.S. Non-Final Office Action, dated May 8, 2015, for U.S. Appl. No. 13/756,837.
U.S. Non-Final Office Action, dated Oct. 20, 2014, for U.S. Appl. No. 13/756,837.
U.S. Notice of Allowance, dated Dec. 26, 2014, for U.S. Appl. No. 13/956,974.
U.S. Office Action (Requirement for Restriction/Election), dated May 9, 2014, for U.S. Appl. No. 13/956,974.
U.S. Office Action, dated Jun. 24, 2015, for U.S. Appl. No. 14/118,136.
U.S. Office Action, dated Sep. 21, 2015, for U.S. Appl. No. 14/107,746.
U.S. Office Action, dated Apr. 17, 2015, for U.S. Appl. No. 13/775,451.
U.S. Office Action, dated Aug. 25, 2014, for U.S. Appl. No. 13/956,974.
"Fundamental of Polymer Chemistry and Physics," edited by Wuji WEI and etc., Chemical Industry Press, Oct. 2011, pp. 59-60 (4 pages total).
English translation of Chinese Office Action for Appl. No. 201480032195.6 dated Jan. 24, 2018.
English translation of the Chinese Office Action, dated Sep. 22, 2017, for Chinese Application No. 201380044153.X.
International Search Report and English translation thereof, dated Jan. 21, 2014, for International Application No. PCT/JP2013/081090.
International Search Report and Written Opinion of the International Searching Authority, issued in PCT/JP2014/079947, dated Jan. 20, 2015.
International Search Report and English translation for PCT/JP2015/070547 (PCT/ISA/210) dated Oct. 6, 2015.
International Search Report, dated Feb. 25, 2014, for International Application No. PCT/JP2013/082409.
International Search Report, issued in PCT/JP2014/063268, dated Aug. 19, 2014.
Jinan Haohua Industry Co., Ltd., "Ethanaminum, N,N,N-trimethyl-2-[(2-methyl-1-oxo-2-propen-1-yl)oxy]-, chloride (1:1),"CAS: 5039-78-1, Product Information Inquiry Description, found online on Dec. 27, 2016, http://guide7932.guidechem.com/pro-show2436647.html.
Odian, "Principles of polymerization," John Wiley & Sons, 4th Ed., 2004, p. 261 (3 pages total).
Placzek et al., "Photosensitizing properties of compounds related to benzophenone,"Acta Dermato-Venereologica, vol. 93, No. 1, 2013, pp. 30-32.
U.S. Office Action, dated Nov. 3, 2016, for U.S. Appl. No. 14/896,096.
Written Opinion of the International Searching Authority and English translation for PCT/JP2015/070547 (PCT/ISA/237) dated Oct. 6, 2015.
Zhang et al., "Corona Radiation Technology," China Textile Press, May 2003, p. 14 (3 pages total).

\* cited by examiner

METHOD FOR MODIFYING SURFACE AND SURFACE MODIFIED ELASTIC BODY

TECHNICAL FIELD

The present invention relates to surface modification methods and surface-modified elastic bodies, such as a gasket for syringes at least part of whose surface is modified by the modification method, a syringe barrel at least part of whose surface is modified by the modification method, and a tire at least part of whose groove surface is modified by the modification method.

BACKGROUND ART

In view of the importance of sealing properties, elastic bodies such as rubber are used in parts which slide while maintaining their sealing performance, for example a gasket which is integrated with a syringe plunger and forms a seal between the plunger and barrel. Unfortunately, such elastic bodies have a slight problem with the sliding properties (see Patent Literature 1). Thus, a sliding property improving agent, for example silicone oil, is applied to the sliding surface. However, a concern has been raised over the potential adverse effects of silicone oil on recently marketed bio-preparations. On the other hand, gaskets not coated with a sliding property improving agent have poor sliding properties and thus do not allow plungers to be smoothly pushed but cause them to pulsate during administration, leading to problems such as an inaccurate injection amount and infliction of pain on patients.

To satisfy the conflicting requirements, sealing properties and sliding properties, a coating technique using a self-lubricating PTFE film has been proposed (see Patent Literature 2). Unfortunately, such PTFE films are generally expensive and increase the production cost of processed products. Thus, the range of applications of these films is limited. Also, products coated with PTFE films might not be reliable when they are used in applications where sliding or the like is repeated and thus durability is required. Furthermore, since PTFE is vulnerable to radiation, the PTFE-coated products unfortunately cannot be sterilized by radiation.

Consideration may also be given to the use in other applications where sliding properties are required in the presence of water. Specifically, water can be delivered without a loss by reducing the fluid resistance of the inner surface of a pre-filled syringe or of the inner surface of a pipe or tube for delivering water, or by increasing or markedly reducing the contact angle with water. Reduction in the surface resistance of the internal/external surfaces of a catheter tube facilitates insertion of the catheter into the body or introduction of a guide wire through the catheter. Drainage of water on wet roads and of snow on snowy roads can be improved by reducing the fluid resistance of the groove surfaces of tires, or by increasing or markedly reducing the contact angle with water. This results in enhanced grip performance and improved hydroplaning performance and therefore better safety. In addition, less adhesion of dirt and dusts can be expected when the sliding resistance of the sidewall surfaces of tires or the walls of buildings is reduced, or when their contact angle with water is increased.

Further advantageous effects can be expected, including, for example: less pressure loss upon delivering water, an aqueous solution or the like through a diaphragm such as a diaphragm pump or valve; easy sliding of skis and snowboards achieved by enhancing the sliding properties of the sliding surfaces thereof; better noticeability of road signs and signboards achieved by enhancing the sliding properties thereof to allow snow to readily slide on the surface; reduction in water resistance or drag on the outer peripheries of ships and less adhesion of bacteria on the outer peripheries, achieved by reducing the sliding resistance of the outer peripheries or by increasing the contact angle with water; and reduction in water resistance or drag of swimsuits achieved by improving the sliding properties of the thread surfaces thereof.

CITATION LIST

Patent Literature

Patent Literature 1: JP 2004-298220 A
Patent Literature 2: JP 2010-142573 A

SUMMARY OF INVENTION

Technical Problem

The present invention aims to solve the above problems and provide methods for surface-modifying a rubber vulcanizate or a thermoplastic elastomer, which can cost-effectively provide a variety of functions, such as remarkable sliding properties or biocompatibility, according to the application. The present invention also aims to provide surface-modified elastic bodies, such as a gasket for syringes at least part of whose surface is modified by the surface modification method, a syringe barrel at least part of whose surface is modified by the surface modification method, and a tire at least part of whose groove surface or sidewall surface is modified by the method.

Solution to Problem

The present invention relates to a method for surface-modifying a rubber vulcanizate or a thermoplastic elastomer as a modification target, the method including: step 1 of forming polymerization initiation points A on a surface of the modification target; step 2 of radically polymerizing a non-functional monomer starting from the polymerization initiation points A to grow non-functional polymer chains; step 3 of washing the modification target on which the non-functional polymer chains are grown; step 4 of forming polymerization initiation points B on a surface of the non-functional polymer chains; and step 5 of radically polymerizing a fluorine-containing functional monomer starting from the polymerization initiation points B to grow fluorine-containing functional polymer chains.

The step 2 preferably includes radically polymerizing a non-functional monomer starting from the polymerization initiation points A by irradiation with LED light having a wavelength of 300 to 450 nm to grow non-functional polymer chains. The step 5 preferably includes radically polymerizing a fluorine-containing functional monomer starting from the polymerization initiation points B by irradiation with LED light having a wavelength of 300 to 450 nm to grow fluorine-containing functional polymer chains.

The step 1 preferably includes adsorbing a photopolymerization initiator A onto a surface of the modification target, optionally followed by irradiation with LED light having a wavelength of 300 to 400 nm, to form polymerization initiation points A from the photopolymerization initiator A on the surface. The step 4 preferably includes adsorbing a photopolymerization initiator B onto a surface of the non-functional polymer chains, optionally followed by irradiation with LED light having a wavelength of 300 to 400 nm, to form polymerization initiation points B from the photopolymerization initiator B on the surface.

The present invention also relates to a method for surface-modifying a rubber vulcanizate or a thermoplastic elastomer as a modification target, the method including: step I of radically polymerizing a non-functional monomer in the presence of a photopolymerization initiator A on a surface of the modification target to grow non-functional polymer chains; step II of washing the modification target on which the non-functional polymer chains are grown; and step III of radically polymerizing a fluorine-containing functional monomer in the presence of a photopolymerization initiator B on a surface of the non-functional polymer chains to grow fluorine-containing functional polymer chains.

Preferably, the photopolymerization initiator is at least one of a benzophenone compound or a thioxanthone compound.

Preferably, the washing is carried out with at least one selected from the group consisting of hot water, steam, and an organic solvent.

Preferably, the rubber vulcanizate or thermoplastic elastomer contains an allylic carbon atom which is adjacent to a double bond.

According to the method, the polymerization is preferably carried out in an inert gas atmosphere.

According to the method, the polymerization is preferably carried out under evacuation.

Preferably, the non-functional monomer is at least one selected from the group consisting of acrylic acid, acrylic acid esters, alkali metal salts of acrylic acid, amine salts of acrylic acid, acrylamide, dimethylacrylamide, diethylacrylamide, isopropylacrylamide, hydroxyethylacrylamide, methoxymethylacrylamide, acryloylmorpholine, methoxyethyl acrylate, hydroxyethyl acrylate, methacrylic acid, methacrylic acid esters, alkali metal salts of methacrylic acid, amine salts of methacrylic acid, methacrylamide, dimethylmethacrylamide, diethylmethacrylamide, isopropylmethacrylamide, hydroxyethylmethacrylamide, methacryloylmorpholine, methoxyethyl methacrylate, hydroxyethyl methacrylate, and acrylonitrile.

Preferably, the fluorine-containing functional monomer is an acrylate or methacrylate containing at least one of the following groups: a fluoroalkyl group, a fluoroalkylether group, and a dimethylsiloxane group.

Preferably, the fluorine-containing functional monomer is a fluorine-containing (meth)acrylic-modified organic silicon compound obtained by addition reaction of a fluorine-containing epoxy-modified organic silicon compound (A) represented by the following formula (1) with an unsaturated monocarboxylic acid (B) containing a (meth)acrylic group:

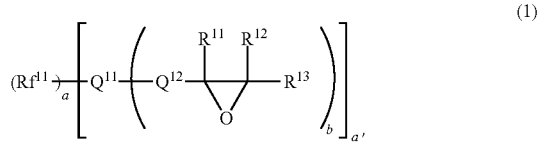

(1)

wherein $Rf^{11}$ is a monovalent or bivalent group having a fluoroalkyl or fluoropolyether structure with a molecular weight of 100 to 40,000; $Q^{11}$ is a (a+b)-valent linking group that contains at least a+b silicon atoms and has a siloxane structure, a non-substituted or halogen-substituted silalkylene structure, a silarylene structure, or a combination of two or more of these structures, and optionally has a cyclic structure; $Q^{12}$ is a bivalent C1-C20 hydrocarbon group optionally having a cyclic structure and optionally interrupted by an ether bond or ester bond; $R^{11}$ to $R^{13}$ are each independently a hydrogen atom or a monovalent C1-C10 hydrocarbon group, the hydrogen atoms of $R^{11}$ to $R^{13}$ may be partially or entirely substituted with halogen atoms, and $R^{11}$ and $R^{12}$ may be joined to form a ring together with the carbon atoms to which $R^{11}$ and $R^{12}$ are attached; when $Rf^{11}$ is monovalent, a' is 1 and a is an integer of 1 to 6, and when $Rf^{11}$ is bivalent, a is 1 and a' is 2; and b is an integer of 1 to 20.

Preferably, $Rf^{11}$ in the formula (1) contains 1 to 500 repeating units represented by the following formula:

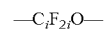

—$C_iF_{2i}O$— wherein i in each unit is independently an integer of 1 to 6.

Preferably, $Q^{11}$ in the formula (1) is represented by either of the following formulae:

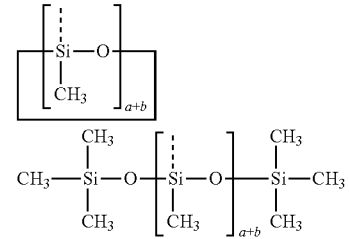

wherein a and b are defined as above, a units and b units are each arranged at random, and the bond indicated by the dashed line in each of a units and b units is attached to $Rf^{11}$ or the group represented by the following formula:

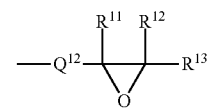

wherein $Q^{12}$ and $R^{11}$ to $R^{13}$ are as defined in the formula (1).

$Rf^{11}$ in the formula (1) is represented by the following formula (3):

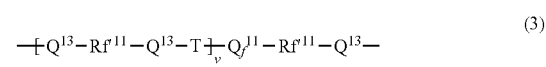

(3)

wherein $Rf^{11}$ is a bivalent perfluoropolyether group having a molecular weight of 300 to 30,000 and optionally internally branched; $Q^{13}$ is a bivalent organic group optionally containing an oxygen, nitrogen, fluorine, or silicon atom, and optionally having a cyclic structure or an unsaturated bond; $Q_f^{11}$ is $Q^{13}$ or a fluorine atom; T is a linking group represented by the following formula (4):

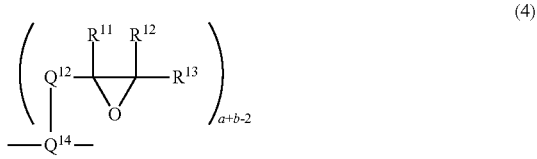

(4)

wherein $R^{11}$ to $R^{13}$, $Q^{12}$, a, and b are as defined in the formula (1), and $Q^{14}$ is a (a+b)-valent linking group that contains at least a+b silicon atoms and has a siloxane structure, a non-substituted or halogen-substituted silalkylene structure, a silarylene structure, or a combination of two or more of these structures; and v is an integer of 0 to 5, and when $Q_f^{11}$ is a fluorine atom, v is 0.

Preferably, the fluorine-containing functional monomer is a mixture of a fluorine-containing epoxy-modified organic silicon compound represented by the following formula and a fluorine-containing (meth)acrylic-modified organic silicon compound represented by the following formula:

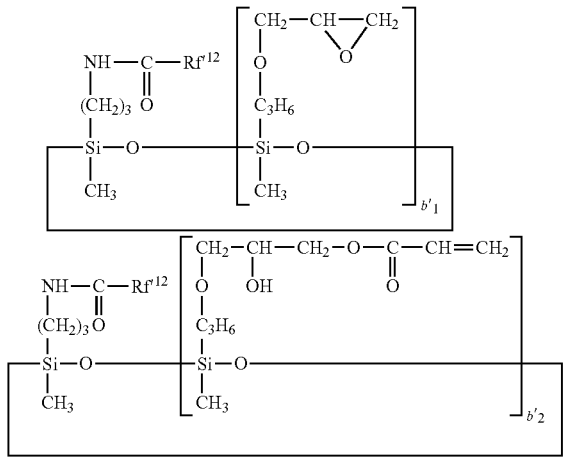

wherein the sum $b'_1+b'_2$ is 2 to 6.5 and $Rf^{12}$ is a group represented by the following formula:

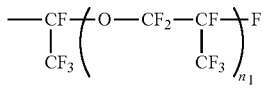

wherein $n_1$ is 2 to 100.

Preferably, the fluorine-containing functional monomer is a polyfunctional (meth)acrylate compound including a cyclic siloxane represented by the following formula:

$$(Rf^{21}R^{21}SiO)(R^4R^{21}SiO)_h$$

wherein $R^{21}$ is a hydrogen atom, a methyl group, an ethyl group, a propyl group, or a phenyl group; $Rf^{21}$ is a fluorine-containing organic group; $R^A$ is a (meth)acrylic group-containing organic group; and h≥2, the polyfunctional (meth)acrylate containing three or more F atoms and three or more Si atoms per molecule.

Preferably, $R^A$ is attached to the Si atom via a Si—O—C bond.

Preferably, $Rf^{21}$ is a group represented by $C_tF_{2t+1}(CH_2)_u$— wherein t is an integer of 1 to 8 and u is an integer of 2 to 10, or a perfluoropolyether-substituted alkyl group.

Preferably, the fluorine-containing functional monomer has an infrared absorption spectrum having strong absorption peaks at around 1045 $cm^{-1}$ and around 1180 $cm^{-1}$, absorption peaks at around 806 $cm^{-1}$ and around 1720 $cm^{-1}$, a weak absorption peak at around 1532 $cm^{-1}$, and a broad and weak absorption peak at around 3350 $cm^{-1}$.

Preferably, the fluorine-containing functional monomer has a $^{13}C$ NMR spectrum in chloroform-d solution having signals at chemical shifts of about 13.01, 14.63, 23.04, 40.13, 50.65, 63.54, 68.97, 73.76, 76.74, 77.06, 77.38, 113.21, 114.11, 116.96, 117.72, 118.47, 128.06, 131.38, 156.46, and 166.02 ppm.

Preferably, the fluorine-containing functional monomer has a $^1H$ NMR spectrum in chloroform-d solution having signals at chemical shifts of about 3.40, 3.41, 3.49, 3.60, 5.26, 5.58, 6.12, 6.14, 6.40, 6.42, and 6.46 ppm.

Preferably, a solution of the non-functional monomer or fluorine-containing functional monomer, or the non-functional monomer or fluorine-containing functional monomer in the liquid state contains a polymerization inhibitor, and is polymerized in the presence of the polymerization inhibitor. Here, the polymerization inhibitor is preferably 4-methylphenol.

Preferably, a length of the entire polymer chain, including the non-functional polymer chain and the fluorine-containing functional polymer chain, is 10 to 50,000 nm.

Preferably, a ratio in length between the non-functional polymer chain and the fluorine-containing functional polymer chain is 50:50 to 99.9:0.1.

The present invention relates to a surface-modified elastic body, which is obtained by the above-described surface modification method.

The present invention relates to a surface-modified elastic body, which is obtained by the above-described surface modification method, the elastic body being required to have sliding properties, low friction or low water resistance in the presence of water or in a dry state.

The present invention relates to a surface-modified elastic body, including a three-dimensional solid body at least part of whose surface is modified by the above-described surface modification method.

The surface-modified elastic body preferably includes a polymer brush.

The present invention relates to a gasket for syringes, at least part of whose surface is modified by the above-described surface modification method.

The present invention relates to a syringe barrel, at least part of whose surface is modified by the above-described surface modification method.

The present invention relates to a tire, at least one of whose groove surface or sidewall surface is partly modified by the above-described surface modification method.

Advantageous Effects of Invention

The present invention relates to a method for surface-modifying a rubber vulcanizate or a thermoplastic elastomer as a modification target, the method including the steps 1 to 5 or the steps I to III, in which washing in the step 3 or II is performed after growing the non-functional polymer chains, and the fluorine-containing functional polymer chains are therefore firmly bonded to the surface of the non-functional polymer chains in the subsequent step. Accordingly, a polymer layer in which the fluorine-containing organic polymer chains are firmly bonded to the outermost surface of the polymer chains is formed, thereby providing desired functions such as remarkable sliding properties. Economically advantageously, the other parts of the polymer chains are formed of a polymer layer comprising the non-functional polymer chains.

DESCRIPTION OF EMBODIMENTS

Figure 1:
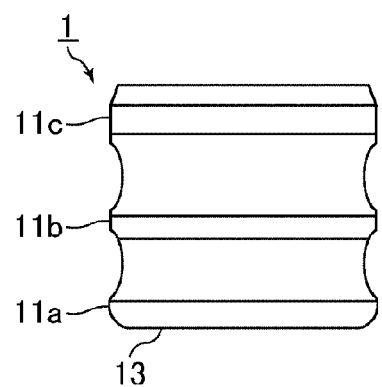
FIG. 1 is an exemplary side view of an embodiment of a gasket for syringes.

The present invention relates to a method for surface-modifying a rubber vulcanizate or a thermoplastic elastomer as a modification target, the method including: step 1 of forming polymerization initiation points A on a surface of the modification target; step 2 of radically polymerizing a non-functional monomer starting from the polymerization initiation points A to grow non-functional polymer chains; step 3 of washing the modification target on which the non-functional polymer chains are grown; step 4 of forming polymerization initiation points B on a surface of the non-functional polymer chains; and step 5 of radically polymerizing a fluorine-containing functional monomer starting from the polymerization initiation points B to grow fluorine-containing functional polymer chains.

To provide a desired function by forming polymer chains on the surface of a rubber vulcanizate or thermoplastic elastomer which usually has large irregularities, it is necessary to form polymer chains having a certain height (length) from the surface with functional polymer chains being disposed on the top. Since functional monomers are usually very expensive, the use of these monomers is economically disadvantageous unless the amount of polymer chains formed from these monomers is the minimum amount required to produce the desired function. In contrast, the present invention provides a surface modification method in which polymer chains are first formed from inexpensive non-functional monomers on the surface of a modification target to build a certain scaffold, and then a fluorine-containing functional monomer is polymerized to build up a minimum amount of functional polymer chains on the scaffold, whereby a functional polymer layer is formed on the outermost surface. Thus, the present invention can very cost-effectively provide surface-modified elastic bodies that are imparted with desired functions, such as sliding properties, biocompatibility, and antibacterial properties.

Moreover, since the fluorine-containing functional monomer used in the present invention has low surface free energy, forming functional polymer chains from the monomer on the outermost surface provides a surface having high sliding properties. In particular, since the functional polymer chains are formed after growing non-functional polymer chains and performing washing treatment, the functional polymer chains are firmly bonded, remarkably improving the sliding properties.

The step 1 includes forming polymerization initiation points A on a surface of a vulcanized rubber or a molded thermoplastic elastomer (modification target).

The rubber vulcanizate or thermoplastic elastomer may suitably contain a carbon atom adjacent to a double bond (i.e., allylic carbon atom).

Examples of rubber as the modification target include diene rubbers such as styrene-butadiene rubber, polybutadiene rubber, polyisoprene rubber, natural rubber, and deproteinized natural rubber; and butyl rubber, halogenated butyl rubber, and silicone rubber which have a degree of unsaturation of a few percent of isoprene units. The butyl rubber or halogenated butyl rubber, if used, is preferably a rubber cross-linked by triazine because the amount of matter extracted from the rubber vulcanizate is small. In this case, the rubber may contain an acid acceptor. Examples of suitable acid acceptors include hydrotalcite and magnesium carbonate.

If other rubbers are used, preferably sulfur vulcanization is performed. In such cases, compounding ingredients commonly used for sulfur vulcanization may be added, such as vulcanization accelerators, zinc oxide, filler, and silane coupling agents. Suitable examples of the filler include carbon black, silica, clay, talc, and calcium carbonate.

The vulcanization conditions for the rubber may be appropriately set. The rubber is preferably vulcanized at 150° C. or higher, more preferably 170° C. or higher, still more preferably 175° C. or higher.

Examples of the thermoplastic elastomer include polymer compounds that have rubber elasticity at room temperature owing to aggregates of plastic components (hard segments) serving as crosslinking points (e.g., thermoplastic elastomers (TPE) such as styrene-butadiene-styrene copolymer); and polymer compounds having rubber elasticity, obtained by mixing a thermoplastic component and a rubber component and dynamically crosslinking the mixture by a cross-linking agent (e.g., thermoplastic elastomers (TPV) such as polymer alloys containing a styrenic block copolymer or olefinic resin and a cross-linked rubber component).

Other examples of suitable thermoplastic elastomers include nylon, polyester, polyurethane, polypropylene, fluoroelastomers such as PTEF, and dynamically cross-linked thermoplastic elastomers thereof. Preferred among dynamically cross-linked thermoplastic elastomers are those obtained by dynamically crosslinking halogenated butyl rubber in a thermoplastic elastomer. This thermoplastic elastomer is preferably nylon, polyurethane, polypropylene, styrene-isobutylene-styrene block copolymer (SIBS), or the like.

The polymerization initiation points A may be formed, for example, by adsorbing a photopolymerization initiator A onto a surface of the modification target. Examples of the photopolymerization initiator A include carbonyl compounds, organic sulfur compounds such as tetraethylthiuram disulfide, persulfides, redox compounds, azo compounds, diazo compounds, halogen compounds, and photoreductive pigments. Carbonyl compounds are especially preferred.

The carbonyl compound as the photopolymerization initiator A is preferably benzophenone or its derivative, and may suitably be a benzophenone compound represented by the following formula:

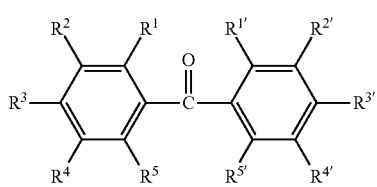

wherein $R^1$ to $R^5$ and $R^{1'}$ to $R^{5'}$ are the same as or different from one another and each represent a hydrogen atom, an alkyl group, a halogen (fluorine, chlorine, bromine, or iodine), a hydroxy group, a primary to tertiary amino group, a mercapto group, or a hydrocarbon group optionally containing an oxygen atom, a nitrogen atom, or a sulfur atom; and any two adjacent groups thereof may be joined to each other to form a cyclic structure together with the carbon atoms to which they are attached.

Specific examples of the benzophenone compound include benzophenone, xanthone, 9-fluorenone, 2,4-dichlorobenzophenone, methyl o-benzoylbenzoate, 4,4'-bis(dimethylamino)benzophenone, and 4,4'-bis(diethylamino)benzophenone. Benzophenone, xanthone, and 9-fluorenone are particularly preferred because then good polymer brushes can be formed.

Other examples of suitable benzophenone compounds include fluorobenzophenone compounds, such as 2,3,4,5,6-pentafluorobenzophenone and decafluorobenzophenone represented by the following formulae.

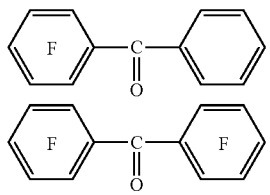

Thioxanthone compounds can also be suitably used as the photopolymerization initiator A because they provide a high polymerization rate and also can easily be adsorbed on and/or reacted with rubber or the like. For example, compounds represented by the following formula can be suitably used.

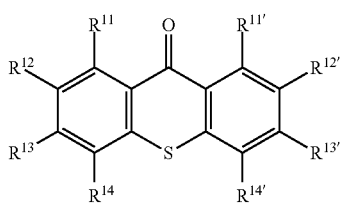

In the formula, $R^{11}$ to $R^{14}$ and $R^{11'}$ to $R^{14'}$ are the same as or different from one another and each represent a hydrogen atom, a halogen atom, an alkyl group, a cyclic alkyl group, an aryl group, an alkenyl group, an alkoxy group, or an aryloxy group.

Examples of thioxanthone compounds represented by the formula include thioxanthone, 2-isopropylthioxanthone, 4-isopropylthioxanthone, 2,3-diethylthioxanthone, 2,4-diethylthioxanthone, 2,4-dichlorothioxanthone, 2-methoxythioxanthone, 1-chloro-4-propoxythioxanthone, 2-cyclohexylthioxanthone, 4-cyclohexylthioxanthone, 2-vinylthioxanthone, 2,4-divinylthioxanthone, 2,4-diphenylthioxanthone, 2-butenyl-4-phenylthioxanthone, 2-methoxythioxanthone, and 2-p-octyloxyphenyl-4-ethylthioxanthone. Preferred among these are the compounds in which one or two, particularly two of the $R^{11}$ to $R^{14}$ and $R^{11'}$ to $R^{14'}$ are substituted with alkyl groups, and more preferred is 2,4-diethylthioxanthone.

The photopolymerization initiator A such as a benzophenone compound or a thioxanthone compound may be adsorbed onto the surface of the modification target by conventionally known methods. In the case of using a benzophenone compound or a thioxanthone compound, for example, the benzophenone compound or thioxanthone compound is dissolved in an organic solvent to prepare a solution; a surface portion of the target to be modified is treated with this solution so that the compound is adsorbed on the surface; and if necessary, the organic solvent is evaporated off by drying, whereby polymerization initiation points are formed. The surface may be treated by any method that allows the solution of the benzophenone compound or the thioxanthone compound to be brought into contact with the surface of the modification target. Suitable methods include application or spraying of the benzophenone compound solution or the thioxanthone compound solution, and immersion into the solution. If only part of the surface needs to be modified, it is sufficient to adsorb the photopolymerization initiator A only onto such part of the surface. In this case, for example, application or spraying of the solution is suitable. Examples of the solvent include methanol, ethanol, acetone, benzene, toluene, methyl ethyl ketone, ethyl acetate, and THF. Acetone is preferred because it does not swell the modification target and it can be rapidly dried and evaporated off.

Moreover, after the surface of the modification target portion is treated with the benzophenone compound solution or the thioxanthone compound solution so that the photopolymerization initiator A is adsorbed on the surface, the surface of the modification target is preferably further irradiated with light so that the polymerization initiator is chemically bonded to the surface. For example, the benzophenone compound or the thioxanthone compound can be fixed on the surface by irradiation with ultraviolet light having a wavelength of 300 to 450 nm, preferably 300 to 400 nm, more preferably 350 to 400 nm. During the step 1 and the fixing as shown by the scheme below, hydrogen is abstracted from the rubber surface and a carbon atom on the rubber surface is then covalently bonded to the carbon atom in C=O of benzophenone while the abstracted hydrogen is bonded to the oxygen atom in C=O to form C—O—H. Moreover, since this hydrogen abstraction reaction selectively occurs on allylic hydrogen atoms in the modification target, the rubber preferably contains a butadiene or isoprene unit that contains an allylic hydrogen atom.

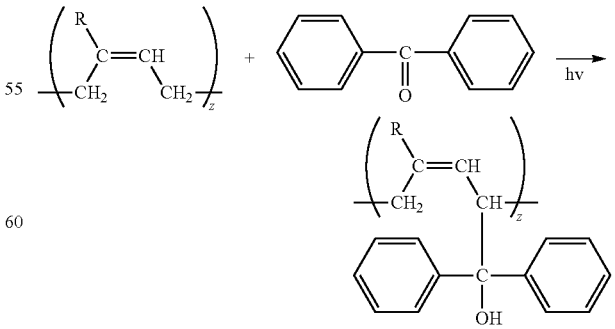

R: Hydrogen or C1-C4 alkyl group

In particular, the polymerization initiator A is preferably formed by treating the surface of the modification target with the photopolymerization initiator A so that the photopolymerization initiator A is adsorbed on the surface, and then irradiating the treated surface with LED light having a wavelength of 300 to 450 nm. Particularly preferably, after the surface of the modification target is treated with the benzophenone compound solution or the thioxanthone compound solution so that the photopolymerization initiator A is adsorbed, the treated surface is further irradiated with LED light having a wavelength of 300 to 450 nm so that the adsorbed photopolymerization initiator A is chemically bonded to the surface. Light having a wavelength of less than 300 nm may cleave molecules of the modification target to give damage. Therefore, preferred is light having a wavelength of 300 nm or greater. More preferred is light having a wavelength of 355 nm or greater because the damage to be given to the modification target is very small. In contrast, light having a wavelength of greater than 450 nm is less likely to activate the polymerization initiator, so that the polymerization reaction is hard to proceed. Therefore, preferred is light having a wavelength of 450 nm or less. Since the polymerization initiator is further activated, more preferred is light having a wavelength of 400 nm or less. The wavelength of LED light is particularly preferably 355 to 380 nm. Here, LED light is preferably used because it has a narrow wavelength range and does not emit light having a wavelength other than the center wavelength. Even in the case of using a mercury lamp or the like, the same effect as that in the case of using LED light can be achieved by cutting light having a wavelength of less than 300 nm with a filter.

The step 2 includes radically polymerizing a non-functional monomer starting from the polymerization initiation points A to grow non-functional polymer chains.

The non-functional monomer in the step 2 refers to a monomer that forms non-functional polymer chains which do not have functions appropriately chosen according to the application or the like. For example, in cases where sliding properties, biocompatibility, anti-bacterial properties or other functions are intended to be provided to the modification target, the non-functional monomer is one which does not provide such functions, and may be appropriately selected in view of economic efficiency or the like.

The non-functional monomer may be appropriately selected from the above-mentioned standpoint. Examples include acrylic acid, acrylic acid esters such as methyl acrylate or ethyl acrylate, alkali metal salts of acrylic acid such as sodium acrylate or potassium acrylate, amine salts of acrylic acid, acrylamide, dimethylacrylamide, diethylacrylamide, isopropylacrylamide, hydroxyethylacrylamide, methoxymethylacrylamide, acryloylmorpholine, methoxyethyl acrylate, hydroxyethyl acrylate, methacrylic acid, methacrylic acid esters such as methyl methacrylate or ethyl methacrylate, alkali metal salts of methacrylic acid such as sodium methacrylate or potassium methacrylate, amine salts of methacrylic acid, methacrylamide, dimethylmethacrylamide, diethylmethacrylamide, isopropylmethacrylamide, hydroxyethylmethacrylamide, methacryloylmorpholine, methoxyethyl methacrylate, hydroxyethyl methacrylate and acrylonitrile. These may be used alone, or two or more thereof may be used in combination.

In the step 2, the non-functional monomer may each be radically polymerized as follows. The non-functional monomer or a solution thereof is applied (sprayed) to the surface of the modification target to which a benzophenone compound, a thioxanthone compound or the like is adsorbed or covalently bonded. Alternatively, the modification target is immersed in the non-functional monomer or a solution thereof. Then, the modification target is irradiated with light, such as ultraviolet light, to allow the radical polymerization (photoradical polymerization) to proceed. Thus, non-functional polymer chains can be grown on the surface of the modification target. Further, after the application, the surface may be covered with a transparent cover of glass, PET, polycarbonate, or other materials, followed by irradiating the covered surface with light, such as ultraviolet light, to allow the radical polymerization (photoradical polymerization) to proceed. Thus, non-functional polymer chains can be grown on the surface of the modification target.

The amounts of the radically polymerizable monomers may be appropriately set depending on, for example, the length of polymer chain to be formed, or the properties to be provided by the chains.

The solvent for application (spraying), the method for application (spraying), the method for immersion, the conditions for irradiation, and the like may be conventionally known materials or methods. The solutions of the radically polymerizable monomers may each be an aqueous solution, or a solution in an organic solvent that does not dissolve the photopolymerization initiator used, such as a benzophenone compound or a thioxanthone compound. Furthermore, a solution of each of the radically polymerizable monomers, or the liquid radically polymerizable monomers may contain a known polymerization inhibitor such as 4-methylphenol.

In the present invention, the radical polymerization of the non-functional monomer is allowed to proceed by light irradiation after the application of a solution of the monomer or the liquid monomer or after the immersion in a solution of the monomer or the liquid monomer. Here, UV light sources with an emission wavelength mainly in the ultraviolet region, such as high-pressure mercury lamps, metal halide lamps, and LED lamps, can be suitably used. The light dose may be appropriately set in view of polymerization time and uniformity of the reaction. Moreover, in order to prevent inhibition of polymerization due to active gas such as oxygen in the reaction vessel, oxygen is preferably removed from the reaction vessel and the reaction solution during or before the light irradiation. Thus, for example, a method may appropriately be employed in which an inert gas, such as nitrogen gas or argon gas, is inserted into the reaction vessel and the reaction solution to discharge active gas such as oxygen from the reaction system and thereby replace the atmosphere in the reaction system with the inert gas, or in which the reaction vessel is evacuated to remove oxygen. Also, in order to prevent inhibition of the reaction due to oxygen or the like, for example, a measure may appropriately be taken in which a UV light source is disposed so that no air layer (oxygen content: 15% or higher) exists between the reaction vessel made of glass, plastics or the like and the reaction solution or the modification target.

In the case of irradiation with ultraviolet light, the ultraviolet light preferably has a wavelength of 300 to 450 nm, more preferably 300 to 400 nm. Such light allows polymer chains to be formed well on the surface of the modification target. The light source may be a high-pressure mercury lamp, an LED with a center wavelength of 365 nm, an LED with a center wavelength of 375 nm, or the like. In particular, preferred is irradiation with LED light having a wavelength of 300 to 400 nm, more preferably LED light having a wavelength of 355 to 380 nm. LEDs or the like which have a center wavelength of 365 nm, which is close to the excitation wavelength 366 nm of benzophenone, are particularly preferred in view of efficiency.

The step 3 includes performing washing treatment on the modification target on which the non-functional polymer chains are grown.

The washing treatment may be carried out by a conventionally known method such as washing by immersion in water. Preferably, the modification target is washed with hot water, steam, or an organic solvent such as a hydrophilic organic solvent (e.g., ethanol). For example, washing treatment under pressure and heat, such as autoclave treatment, is preferably employed.

In relation to the conditions for the washing treatment, the pressure is preferably 0.1 to 0.5 MPa, more preferably 0.15 to 0.4 MPa. The temperature is preferably 50° C. to 150° C., more preferably 100° C. to 140° C., still more preferably 110° C. to 140° C. The time is preferably 20 to 1000 minutes, more preferably 30 to 500 minutes. The washing treatment under the above conditions allows the functional polymer chains to be firmly bonded, thereby remarkably improving the performance such as sliding properties.

The step 4 includes forming polymerization initiation points B on the surface of the non-functional polymer chains.

The polymerization initiation points B are formed by a method similar to the method employed in the step 1, such as adsorbing anew a photopolymerization initiator B on the surface of the obtained non-functional polymer chains and optionally further allowing the photopolymerization initiator B to be chemically bonded. Here, the photopolymerization initiator B may be the same compound as that used as the photopolymerization initiator A.

The step 5 includes radically polymerizing a fluorine-containing functional monomer starting from the polymerization initiation points B to grow fluorine-containing functional polymer chains.

The fluorine-containing functional monomer refers to a monomer that forms fluorine-containing functional polymer chains which exert desired functions. Examples thereof include fluorine-containing (meth)acrylic-modified organic silicon compounds and cyclic siloxane. The fluorine-containing functional monomer can provide sliding properties or the like.

The fluorine-containing functional monomer may suitably be, for example, an acrylate or methacrylate containing a fluoroalkyl group, a fluoroalkylether group, and/or a dimethylsiloxane group.

The fluorine-containing functional monomer is also preferably, for example, a fluorine-containing (meth)acrylic-modified organic silicon compound prepared by addition reaction of a fluorine-containing epoxy-modified organic silicon compound (A) represented by the following formula (1) with an unsaturated monocarboxylic acid (B) containing a (meth)acrylic group:

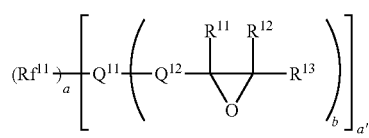
(1)

wherein $Rf^{11}$ is a monovalent or bivalent group having a fluoroalkyl or fluoropolyether structure with a molecular weight of 100 to 40,000; $Q^{11}$ is a (a+b)-valent linking group that contains at least a+b silicon atoms and has a siloxane structure, a non-substituted or halogen-substituted silalkylene structure, a silarylene structure, or a combination of two or more of these structures, and optionally has a cyclic structure; $Q^{12}$ is a bivalent C1-C20 hydrocarbon group optionally having a cyclic structure and optionally interrupted by an ether bond (—O—) or an ester bond (—COO—); $R^{11}$ to $R^{13}$ are each independently a hydrogen atom or a monovalent C1-C10 hydrocarbon group, the hydrogen atoms of $R^{11}$ to $R^{13}$ may be partially or entirely substituted with halogen atoms, and $R^{11}$ and $R^{12}$ may be joined to form a ring together with the carbon atoms to which $R^{11}$ and $R^{12}$ are attached; when $Rf^{11}$ is monovalent, a' is 1 and a is an integer of 1 to 6, and when $Rf^{11}$ is bivalent, a is 1 and a' is 2; and b is an integer of 1 to 20.

Specifically, $Q^{11}$ in the formula (1) representing the fluorine-containing epoxy-modified organic silicon compound (A) may be a group having a structure shown below.

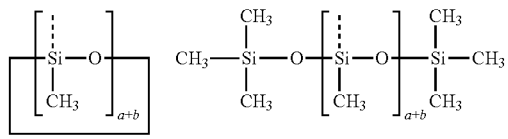

Here, a and b in the formula are as defined above and each preferably an integer of 1 to 4, and the sum a+b is preferably an integer of 3 to 5. Moreover, a units and b units are each arranged at random, and the bond indicated by the dashed line in each of a units and b units is attached to $Rf^{11}$ or the group represented by the following formula:

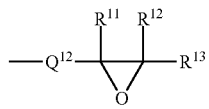

wherein $Q^{12}$ and $R^{11}$ to $R^{13}$ are as defined above.

In the formula (1), $Q^{12}$ is preferably a bivalent hydrocarbon group having a carbon number of 2 to 15. Examples of the specific structure of $Q^{12}$ include —CH$_2$CH$_2$—, —CH$_2$CH(CH$_3$)—, and —CH$_2$CH$_2$CH$_2$OCH$_2$—.

$R^{11}$ to $R^{13}$ are each preferably a monovalent hydrocarbon group having a carbon number of 1 to 8. Specific examples of $R^{11}$ to $R^{13}$ include a hydrogen atom, alkyl groups such as methyl, ethyl, and propyl, and cycloalkyl groups such as cyclopentyl and cyclohexyl.

Examples of the group represented by the formula including a combination of $R^{11}$ to $R^{13}$ and $Q^{12}$ as described above include the following groups.

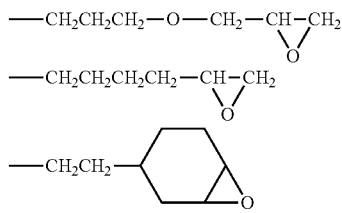

In the formula (1), $Rf^{11}$ preferably has a molecular weight of 500 to 20,000. $Rf^{11}$ is preferably a group containing 1 to 500 repeating units represented by —C$_i$F$_{2i}$O— wherein i in each unit is independently an integer of 1 to 6. The number of repeating units is preferably 2 to 400, more preferably 4 to 200. In the present invention, the molecular weight is a number average molecular weight calculated from the ratio of the terminal structure and the main chain structure based on $^1$H-NMR and $^{19}$F-NMR.

Examples of $Rf^{11}$ in the formula (1) include a group represented by the following formula (3):

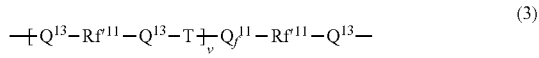
(3)

wherein $Rf^{11}$ is a bivalent perfluoropolyether group having a molecular weight of 300 to 30,000 and optionally internally branched; $Q^{13}$ is a bivalent organic group optionally containing an oxygen, nitrogen, fluorine, or silicon atom, and optionally having a cyclic structure or an unsaturated bond; $Q_f^{11}$ is $Q^{13}$ or a fluorine atom; T is a linking group represented by the following formula (4):

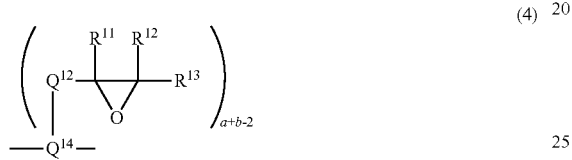
(4)

wherein $R^{11}$ to $R^{13}$, $Q^{12}$, a, and b are as defined in the formula (1), and $Q^{14}$ is a (a+b)-valent linking group that contains at least a+b silicon atoms and has a siloxane structure, a non-substituted or halogen-substituted silalkylene structure, a silarylene structure, or a combination of two or more of these structures; and v is an integer of 0 to 5, and when $Q_f^{11}$ is a fluorine atom, v is 0.

In the formula (3), $Rf^{11}$ preferably has a molecular weight of 500 to 20,000. Specific examples of $Rf^{11}$ include bivalent perfluoropolyether groups represented by the following formulae:

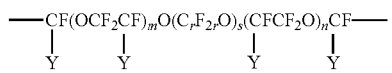

wherein each Y is independently F or a $CF_3$ group, r is an integer of 2 to 6, m and n are each independently an integer of 0 to 200, preferably 0 to 100, provided that the sum m+n is an integer of 2 to 200, preferably 3 to 150, s is an integer of 0 to 6, and repeating units may be each arranged at random; and —$C_jF_{2j}(OCF_2CF_2)_kOC_jF_{2j}$— wherein j is an integer of 1 to 3, and k is an integer of 1 to 200, preferably 1 to 60.

Examples of $Q^{13}$ in the formula (3) include groups represented by the following formulae. In the formula, Ph represents a phenyl group.

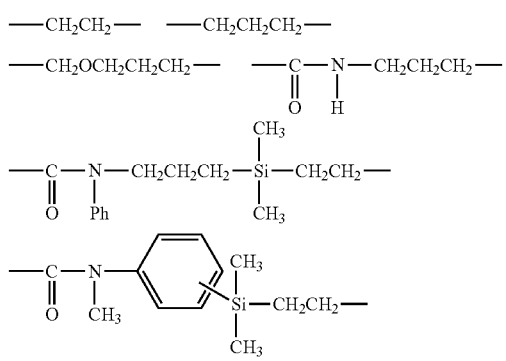

In the formula (1), a is preferably an integer of 1 to 3 when $Rf^{11}$ is monovalent. In that case, b is preferably an integer of 1 to 6. Moreover, the sum a+b is preferably an integer of 3 to 6.

Specific examples of $Rf^{11}$ in the formula (1) include groups shown below:

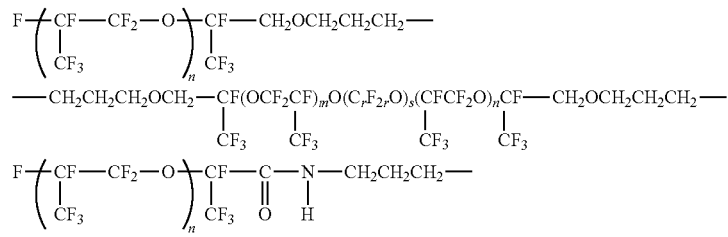

wherein m, n, r, and s are as defined above.

Specific examples of the fluorine-containing epoxy-modified organic silicon compound (A) include the following compounds:

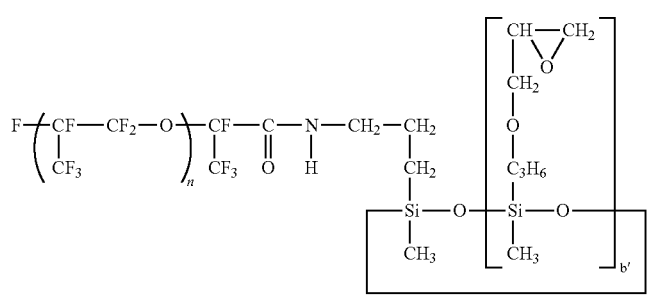

-continued

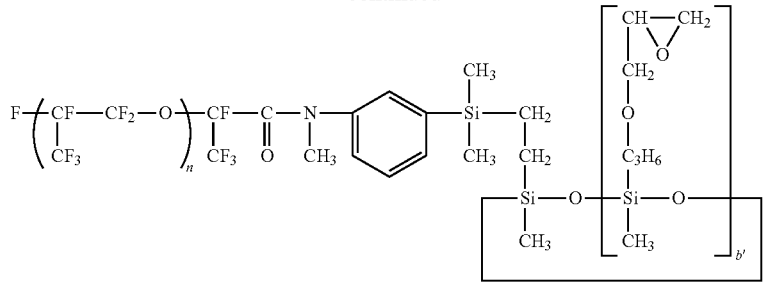

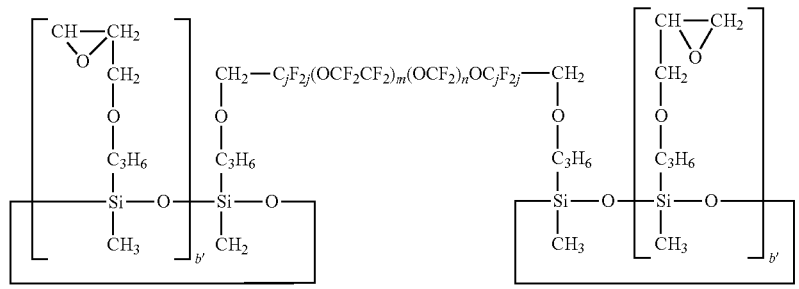

wherein j, m, and n are as defined above, and b' is an integer of 1 to 8.

These fluorine-containing epoxy-modified organic silicon compounds may be used alone, or two or more of these may be used in combination.

The unsaturated monocarboxylic acid (B) containing a (meth)acrylic group is preferably acrylic acid or methacrylic acid, and may be acrylic acid or methacrylic acid in which hydrogen atoms are partially halogenated with halogen atoms (e.g., chlorine, fluorine), such as 2-chloroacrylic acid, 2-(trifluoromethyl)acrylic acid, or 2,3,3-trifluoroacrylic acid. Moreover, those prepared by protecting any of these carboxylic acids with an allyl group, a silyl group, or the like may be used. These unsaturated monocarboxylic acids may be used alone, or two or more of these may be used in combination.

The fluorine-containing (meth)acrylic-modified organic silicon compound in the present invention is obtained by reacting an epoxy group in the fluorine-containing epoxy-modified organic silicon compound (A) with a carboxyl group in the unsaturated monocarboxylic acid (B) containing a (meth)acryl group, and specific examples thereof include compounds shown below.

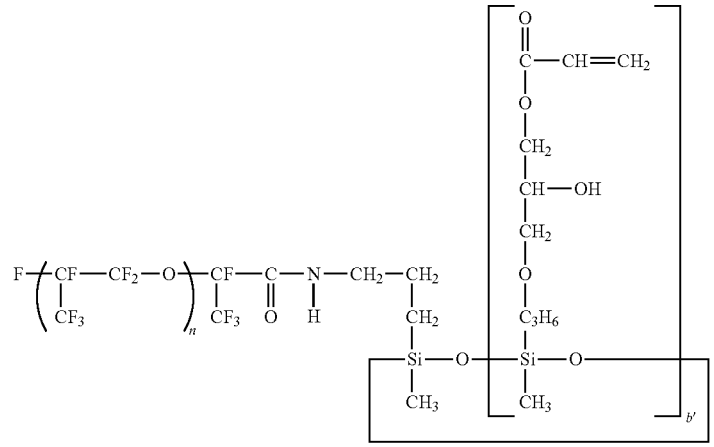

-continued

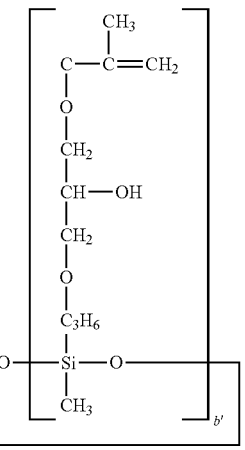
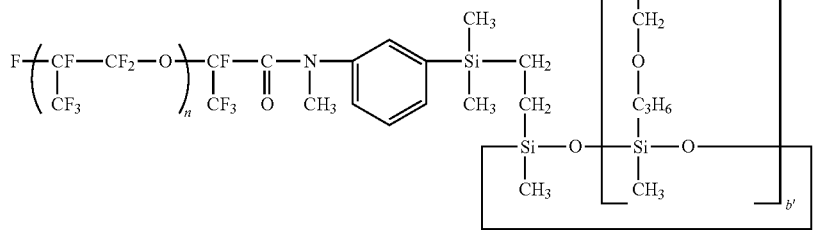

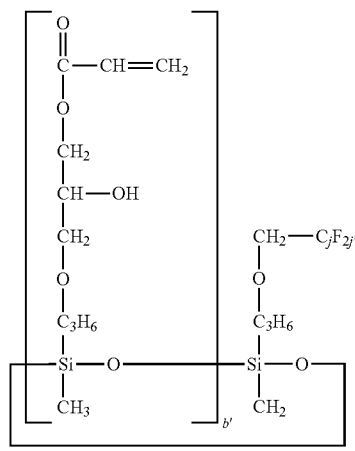
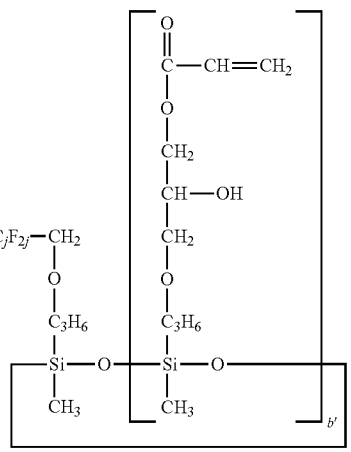

In the formulae, j, m, n, and b' are as defined above.

In the present invention, the fluorine-containing functional monomer may suitably be a mixture of a fluorine-containing epoxy-modified organic silicon compound as mentioned in the above specific examples and a fluorine-containing (meth)acrylic-modified organic silicon compound as mentioned in the above specific examples. Particularly preferred is a mixture of a fluorine-containing epoxy-modified organic silicon compound and a fluorine-containing (meth)acrylic-modified organic silicon compound which are represented by the formulae below. The effect of the present invention can be sufficiently achieved by use of this.

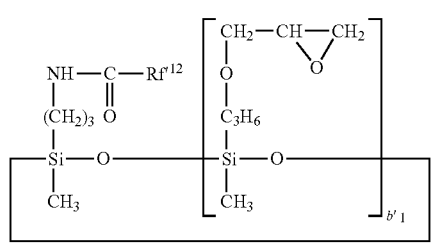

-continued

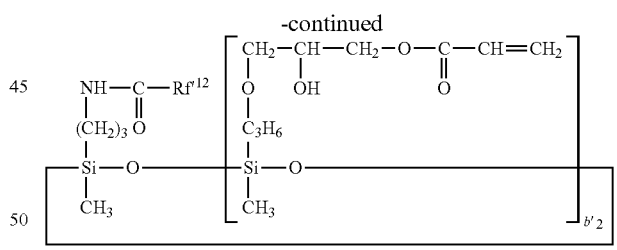

In the formulae, the sum $b'_1 + b'_2$ is 2 to 6.5 and $Rf'^{12}$ is a group shown below:

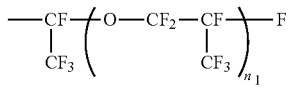

wherein $n_1$ is 2 to 100.

The fluorine-containing functional monomer may be a polyfunctional (meth)acrylate compound including a cyclic siloxane represented by the formula:

$(Rf^{21}R^{21}SiO)(R^4R^{21}SiO)_h$ wherein $R^{21}$ is a hydrogen atom, a methyl group, an ethyl group, a propyl group, or a phenyl group, $Rf^{21}$ is an organic group containing a fluorine atom, and $R^4$ is an organic group containing a (meth)acrylic group, and h≥2, the polyfunctional (meth)acrylate compound containing three or more F atoms and three or more Si atoms per molecule.

In the polyfunctional (meth)acrylate compound, examples of the $Rf^{21}$ include a group represented by $C_tF_{2t+1}(CH_2)_u$— wherein t is an integer of 1 to 8 and u is an integer of 2 to 10, and a perfluoropolyether-substituted alkyl group. Specific examples thereof include $CF_3C_2H_4$—, $C_4F_9C_2H_4$—, $C_4F_9C_3H_6$—, $C_8F_{17}C_2H_4$—, $C_8F_{17}C_3H_6$—, $C_3F_7C(CF_3)_2C_3H_6$—, $C_3F_7OC(CF_3)FCF_2OCF_2CF_2C_3H_6$—, $C_3F_7OC(CF_3)FCF_2OC(CF_3)FC_3H_6$—, and $CF_3CF_2CF_2OC(CF_3)FCF_2OC(CF_3)FCONHC_3H_6$—.

Specific examples of $R^4$ include $CH_2$=CHCOO—, $CH_2$=C(CH_3)COO—, $CH_2$=CHCOOC_3H_6—, $CH_2$=C(CH_3)COOC_3H_6—, $CH_2$=CHCOOC_2H_4O—, and $CH_2$=C(CH_3)COOC_2H_4O—. Further, $R^4$ is preferably attached to the Si atom via a Si—O—C bond. In the formula, h is preferably 3≤h≤5.

The polyfunctional (meth)acrylate compound contains 3 or more F atoms and 3 or more Si atoms per molecule, and preferably contains 3 to 17 F atoms and 3 to 8 Si atoms.

Specific examples of the polyfunctional (meth)acrylate compound include compounds shown below.

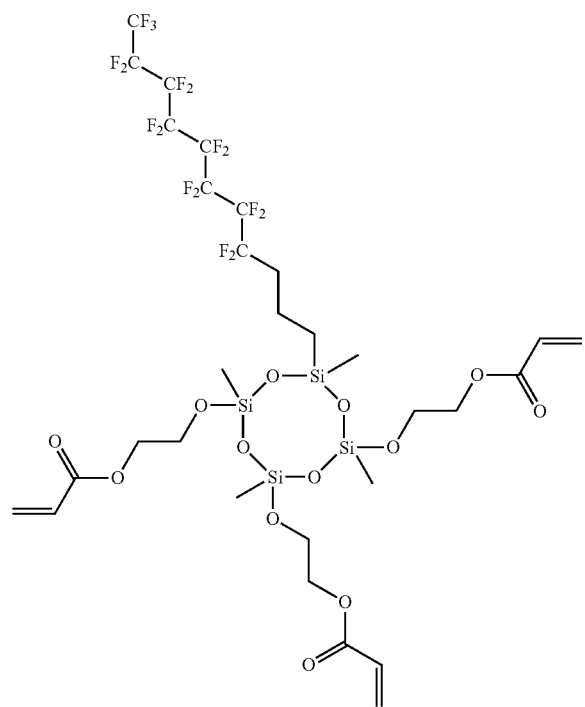

-continued

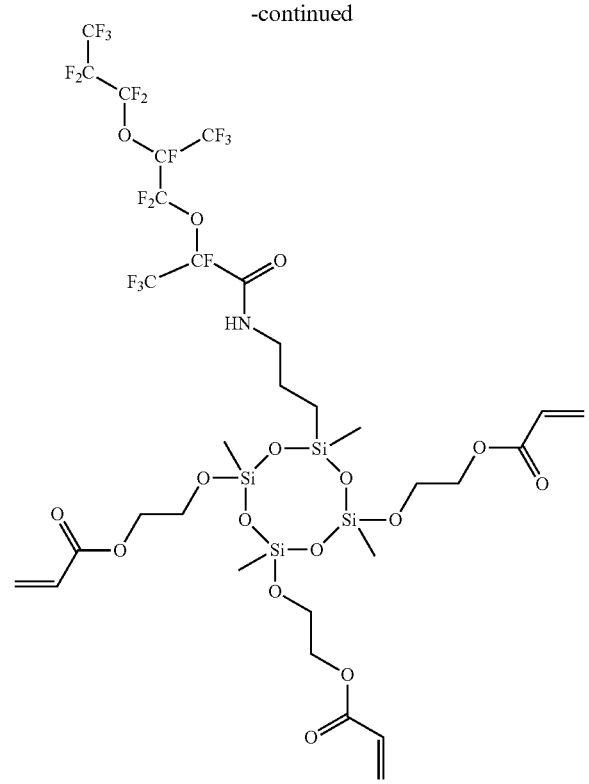

The fluorine-containing functional monomer used in the present invention preferably has an infrared absorption spectrum having absorption peaks at around 1045 cm$^{-1}$, around 1180 cm$^{-1}$, around 806 cm$^{-1}$, around 1720 cm$^{-1}$, around 1532 cm$^{-1}$, and around 3350 cm$^{-1}$. The infrared absorption spectrum particularly preferably has strong absorption peaks at around 1045 cm$^{-1}$ and around 1180 cm$^{-1}$, absorption peaks at around 806 cm$^{-1}$ and around 1720 cm$^{-1}$, a weak absorption peak at around 1532 cm$^{-1}$, and a broad and weak absorption peak at around 3350 cm$^{-1}$. In this case, the fluorine-containing functional polymer chains formed are excellent in sliding properties or the like.

Preferably, the fluorine-containing functional monomer has a $^{13}$C NMR spectrum in chloroform-d (deuterochloroform) solution having signals at chemical shifts of about 13.01, 14.63, 23.04, 40.13, 50.65, 63.54, 68.97, 73.76, 76.74, 77.06, 77.38, 113.21, 114.11, 116.96, 117.72, 118.47, 128.06, 131.38, 156.46, and 166.02 ppm.

Preferably, the fluorine-containing functional monomer has a $^1$H NMR spectrum in chloroform-d (deuterochloroform) solution having signals at chemical shifts of about 3.40, 3.41, 3.49, 3.60, 5.26, 5.58, 6.12, 6.14, 6.40, 6.42, and 6.46 ppm.

The fluorine-containing functional monomer may be radically polymerized, for example, by a method similar to the method of radically polymerizing the non-functional monomer in the step 2.

The present invention also encompasses a method for surface-modifying a rubber vulcanizate or a thermoplastic elastomer as a modification target, the method including: step I of radically polymerizing a non-functional monomer in the presence of a photopolymerization initiator A on a surface of the modification target to grow non-functional polymer chains; step II of washing the modification target on which the non-functional polymer chains are grown; and step III of radically polymerizing a fluorine-containing functional monomer in the presence of a photopolymerization initiator B on a surface of the non-functional polymer chains to grow fluorine-containing functional polymer chains. Specifically, a non-functional monomer is radically polymerized, using a non-functional polymer chains, and the modification target with the non-functional polymer chains grown thereon is washed. Further, a fluorine-containing functional monomer is radically polymerized, using a photopolymerization initiator B as an initiator, to extend the polymer chains to form fluorine-containing functional polymer chains. In this manner, a surface-modified elastic body with a fluorine-containing functional polymer layer formed on the outermost surface is produced. Since functional polymer chains are formed after growing non-functional polymer chains and performing the washing treatment, the functional polymer chains are firmly bonded, remarkably improving the sliding properties.

Preferably, the step I includes radically polymerizing a non-functional monomer starting from the polymerization initiation points A formed by the photopolymerization initiator A on the surface of the modification target, to grow non-functional polymer chains, and the step III includes radically polymerizing a fluorine-containing functional monomer starting from the polymerization initiation points B formed by the photopolymerization initiator B on the surface of the non-functional polymer chains, to grow fluorine-containing functional polymer chains. For example, in the step I, the surface of the modification target is brought into contact with the photopolymerization initiator A and the non-functional monomer, and then irradiated with LED light having a wavelength of 300 to 450 nm so that the photopolymerization initiator A forms polymerization initiation points A and, at the same time, the non-functional monomer is radically polymerized starting from the polymerization initiation points A to grow non-functional polymer chains. In the step III, the surface of the non-functional polymer chains is brought into contact with the photopolymerization initiator B and the fluorine-containing functional monomer, and then irradiated with LED light having a wavelength of 300 to 450 nm so that the photopolymerization initiator B forms polymerization initiation points B and, at the same time, the fluorine-containing functional monomer is radically polymerized starting from the polymerization initiation points B to grow fluorine-containing functional polymer chains.

The non-functional monomer in the step I and the fluorine-containing functional monomer in the step III may each be radically polymerized as follows. A solution of the non-functional monomer or fluorine-containing functional monomer or the liquid non-functional monomer or fluorine-containing functional monomer which contains the photopolymerization initiator A or B, such as a benzophenone compound or a thioxanthone compound is applied (sprayed) to the surface of the modification target or the modification target on which non-functional polymer chains are formed. Alternatively, the modification target or the modification target on which non-functional polymer chains are formed is immersed in a solution of the non-functional monomer or fluorine-containing functional monomer or the liquid non-functional monomer or fluorine-containing functional monomer which contains the photopolymerization initiator A or B such as a benzophenone compound or a thioxanthone compound. Then, the modification target is irradiated with light, such as ultraviolet light, to allow the radical polymerization (photoradical polymerization) of the corresponding monomer to proceed. Thus, non-functional polymer chains and fluorine-containing functional chains can be grown in this order on the surface of the modification target. In another method, the surface may be covered with a transparent sheet of glass, PET, polycarbonate, or the like, followed by irradiating the covered surface with light, such as ultraviolet light. Similarly to the above, a reducing agent and an antioxidant material may be added. The solvent for application (spraying), the method for application (spraying), the method for immersion, the conditions for irradiation, and the like may be above-mentioned known materials or methods.

The washing method in the step II is suitably a method similar to that employed in the step 3.

Moreover, the polymer chains including fluorine-containing functional polymer chains formed provide excellent sliding properties and excellent durability while maintaining good sealing properties. The formed polymer chains preferably each have a polymerization degree of 20 to 200,000, more preferably 350 to 50,000.

The length of the entire polymer chain, including the non-functional polymer chain and the fluorine-containing functional polymer chain is preferably 10 to 50,000 nm, more preferably 100 to 50,000 nm. If the length is shorter than 10 nm, good sliding properties tend not to be achieved. If the length is longer than 50,000 nm, a further improvement in sliding properties cannot be expected while the cost of raw materials tends to increase due to the use of the expensive monomer. In addition, surface patterns generated by the surface treatment tend to be visible to the naked eyes and thereby spoil the appearance and decrease sealing properties.

Regarding the entire polymer chain, the ratio in length between the non-functional polymer chain and the fluorine-containing functional polymer chain [(length of non-functional polymer chain):(length of fluorine-containing functional polymer chain)] is preferably 50:50 to 99.9:0.1, more preferably 90:10 to 99.5:0.5. If the length of the fluorine-containing functional polymer chain is shorter than 1%, desired functions may not be provided, while if it exceeds 50%, there tends to be an economic disadvantage.

In the step 2 and step I, two or more types of non-functional monomers may simultaneously be radically polymerized starting from the polymerization initiation points A. In the step 5 and step III, two or more type of fluorine-containing functional monomers may simultaneously be radically polymerized starting from the polymerization initiation points B. Moreover, two or more layers of non-functional or fluorine-containing functional polymer chains may be stacked. Furthermore, multiple types of polymer chains may be grown on the surface of the modification target. In the surface modification method of the present invention, the polymer chains may be cross-linked to one another. In this case, the polymer chains may be cross-linked to one another by ionic crosslinking, crosslinking by a hydrophilic group containing an oxygen atom, or crosslinking by a halogen group such as iodide.

The surface modification method may be applied to a rubber vulcanizate or a thermoplastic elastomer to prepare a surface-modified elastic body. For example, surface-modified elastic bodies that are excellent in sliding properties in the presence of water or in a dry state can be prepared. Such surface-modified elastic bodies are also excellent in that they have low friction and low water resistance or drag. Moreover, the method may be applied to at least a part of a three-dimensional solid body (e.g. elastic body) to prepare a surface-modified elastic body with modified properties. Furthermore, preferred examples of such surface-modified elastic bodies include polymer brushes. The polymer brush as used herein means an assembly of graft polymer molecules obtained in the "grafting from" approach by surface-initiated living radical polymerization. The graft chains are preferably oriented in a direction substantially vertical to the surface of the modification target because then entropy is reduced and thus the molecular mobility of the graft chains is reduced to provide sliding properties. Moreover, semidilute or concentrated brushes which have a brush density of 0.01 chains/nm$^2$ or higher are preferred.

Furthermore, the surface modification method may be applied to a rubber vulcanizate or a thermoplastic elastomer to prepare a gasket for syringes at least part of whose surface is modified and a syringe barrel at least part of whose surface is modified. Preferably, at least the sliding portion of the surface of the gasket or syringe barrel is modified. The entire surface of the gasket or syringe barrel may be modified.

FIG. 1 is an exemplary side view of an embodiment of a gasket for syringes. A gasket 1 shown in FIG. 1 has three circular protruding portions 11a, 11b and 11c which continuously protrude along the circumferential direction on the outer periphery that is to be in contact with the inner periphery of a syringe barrel. Examples of portions of the gasket 1 to which the surface modification can be applied include: (1) the surfaces of protruding portions to be in contact with a syringe barrel, such as the circular protruding portions 11a, 11b and 11c; (2) the entire side surface including the circular protruding portions 11a, 11b and 11c; and (3) both the entire side surface and a bottom surface 13.

Figure 2:
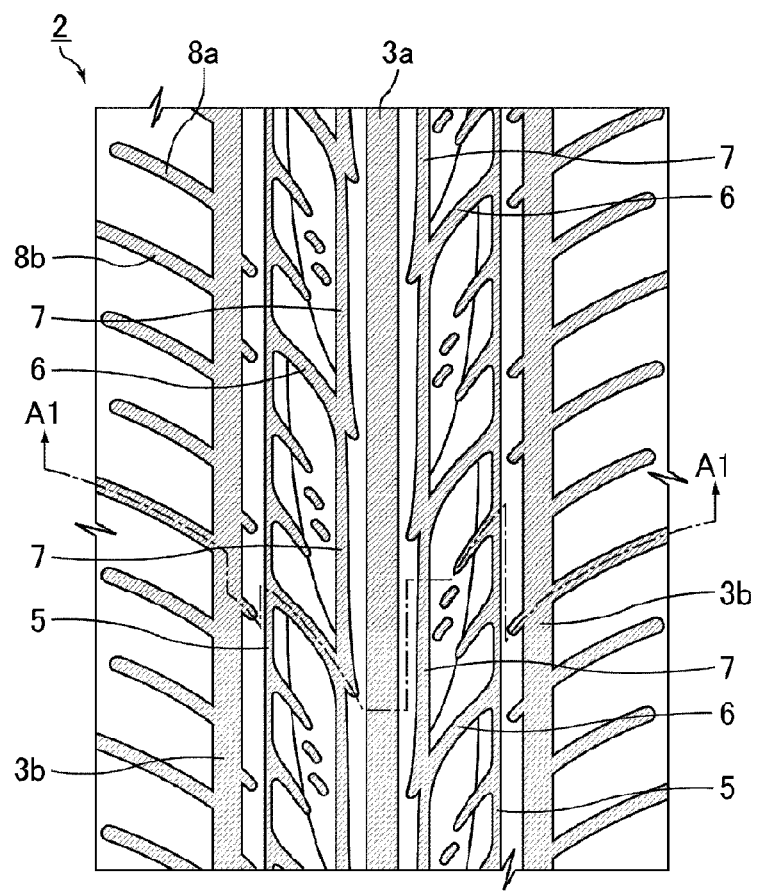
FIG. 2 is an exemplary development view of a tread portion of a pneumatic tire (the whole tire is not shown).
Figure 3:
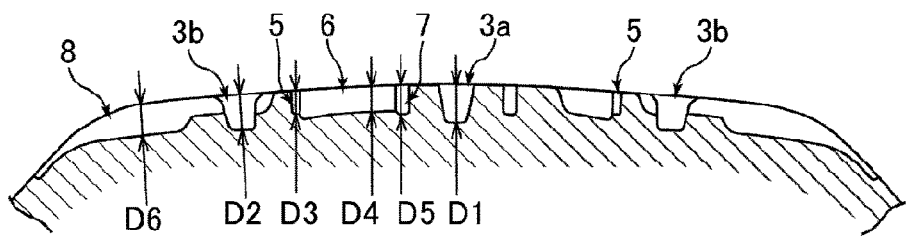
FIG. 3 is an exemplary A1-A1 cross-sectional view of FIG. 2.
Figure 4:
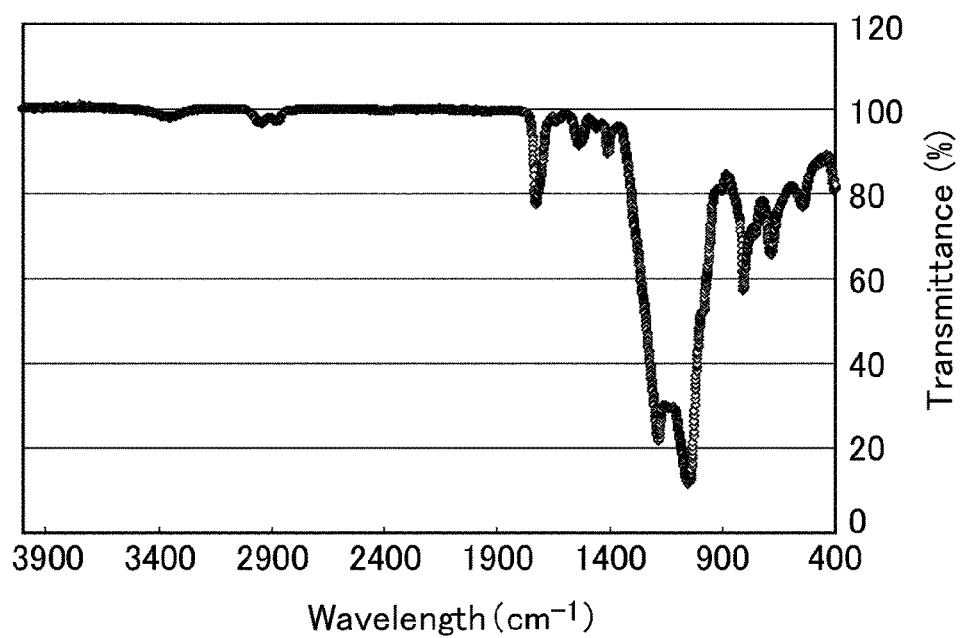
FIG. 4 is an infrared absorption spectrum of a fluorine-containing functional monomer solution (Shin-Etsu Chemical Co., Ltd., KY-1203) used in Example 1.
Figure 5:
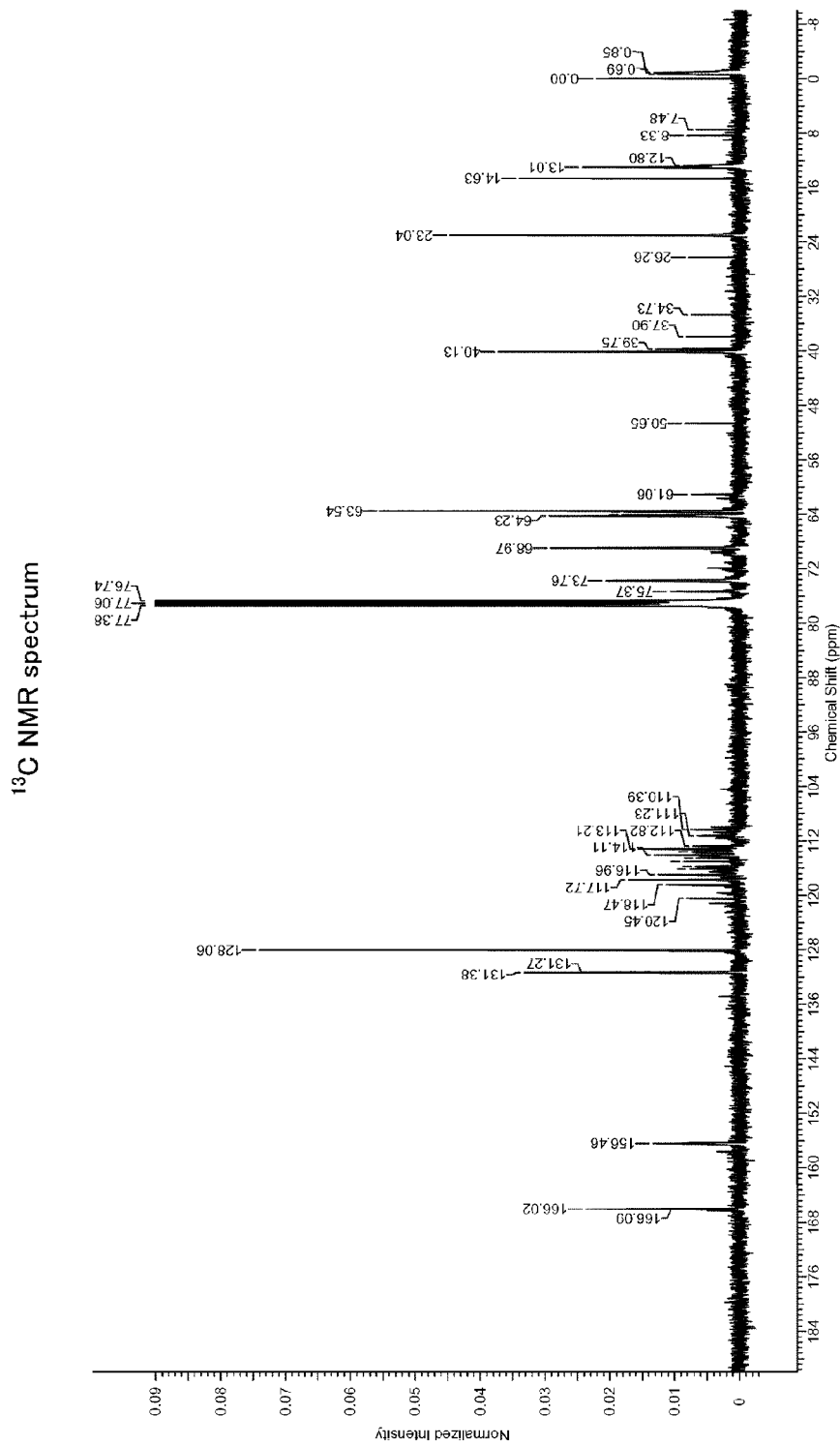
FIG. 5 is a $^{13}$C-NMR spectrum of the fluorine-containing functional monomer solution (Shin-Etsu Chemical Co., Ltd., KY-1203) used in Example 1.
Figure 6:
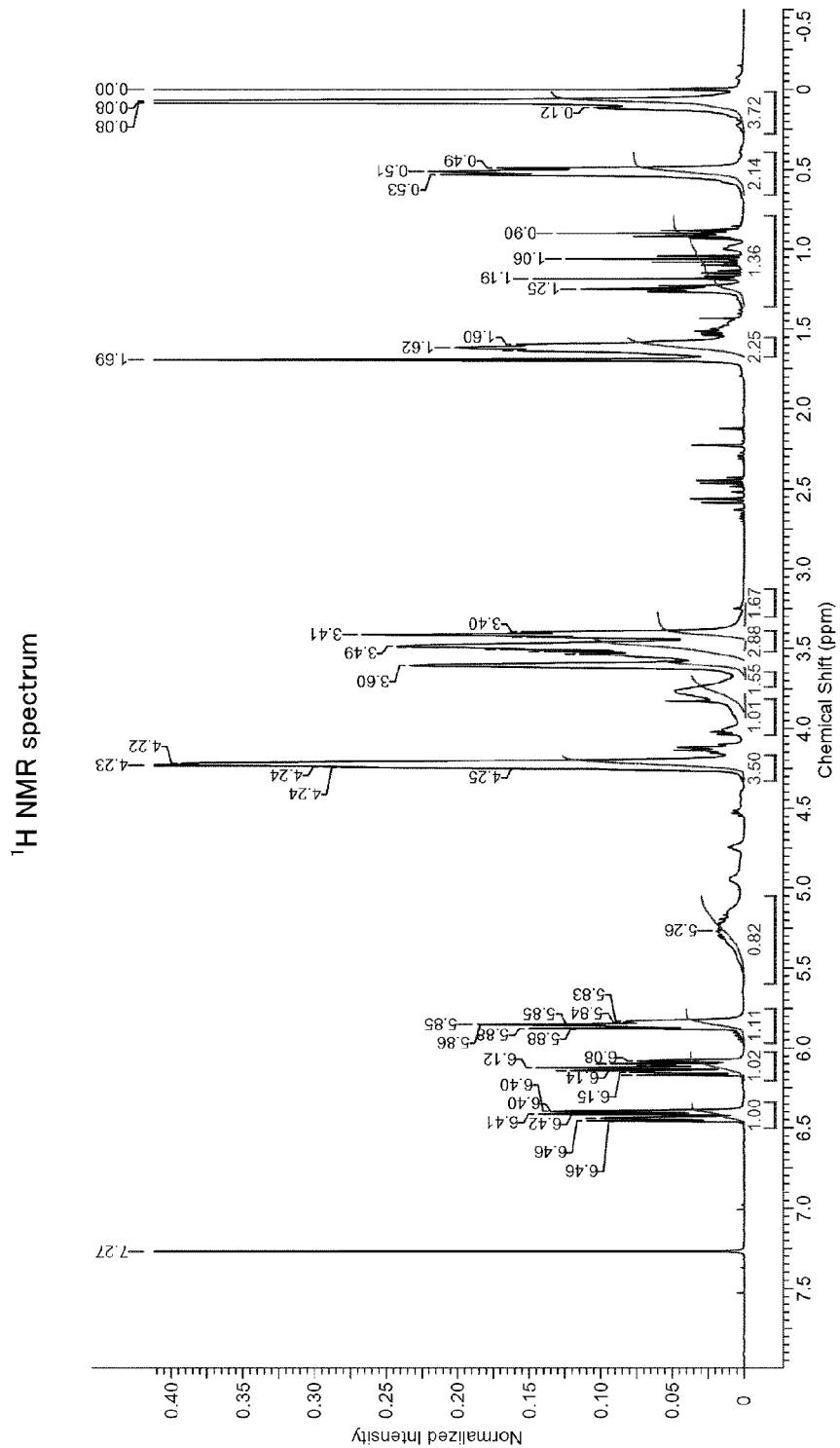
FIG. 6 is a $^{1}$H-NMR spectrum of the fluorine-containing functional monomer solution (Shin-Etsu Chemical Co., Ltd., KY-1203) used in Example 1.

Furthermore, if the surface modification method is applied to the grooves formed on the tread of tires for use on vehicles such as passenger cars to create a polymer brush on the grooves, the fluid resistance of the groove surface on wet or snowy roads is reduced, and the contact angle with water is increased. Thus, the abilities to remove and drain water or snow can be enhanced, resulting in improved grip performance. FIG. 2 is an exemplary development view of a tread portion 2 of a pneumatic tire (the whole tire is not shown). FIG. 3 is an exemplary A1-A1 cross-sectional view of FIG. 2.

In FIGS. 2 and 3, a longitudinal center groove 3a (groove depth D1) and longitudinal shoulder grooves 3b (groove depth D2) are straight grooves linearly extending in the circumferential direction of the tire. Such straight grooves can contribute to low drainage resistance and high drainage performance during straight travelling.

The pneumatic tire also has fine grooves 5 (groove depth D3) extending in the tire circumferential direction on the side of the longitudinal shoulder groove 3b; beveled intermediate grooves 6 (groove depth D4) extending with an inclination from the fine groove 5 toward the longitudinal center groove 3a; connecting grooves 7 (groove depth D5) located inward of the fine groove 5 in the axis direction of the tire and connecting the beveled intermediate grooves 6 next to one another in the circumferential direction of the tire; lateral shoulder grooves 8, 8a and 8b (groove depth D6) extending from the longitudinal shoulder groove 3b toward the outside of the tire; and the like. These grooves can also contribute to drainage performance. If the method is applied to these grooves, the above-mentioned effects can be achieved. If the method is applied to the sidewall surface, the effect of inhibiting adhesion of dirt and dusts is expected to be achieved.

EXAMPLES

The following will describe the present invention in more detail referring to non-limiting examples.

Example 1

A chlorobutyl rubber (degree of unsaturation: 1 to 2%) containing isoprene units was cross-linked by triazine to prepare a vulcanized rubber gasket (vulcanized at 180° C. for 10 minutes), which was then immersed in a 3 wt % solution of benzophenone in acetone so that benzophenone was adsorbed onto the surface of the rubber vulcanizate, followed by drying. Then the surface of the vulcanized rubber gasket was irradiated with LED-UV light having a wavelength of 365 nm for 10 minutes to chemically bond benzophenone to the surface. Thereafter, the surface was washed with acetone to remove unreacted benzophenone. The resulting rubber vulcanizate was taken out and dried.

The dried vulcanized rubber gasket was immersed in an aqueous acrylic acid solution (2.5 M, 18 g of acrylic acid dissolved in 100 mL of water) in a glass reaction vessel. Then the gasket was irradiated with LED-UV light having a wavelength of 365 nm for one hour in an argon gas atmosphere to cause radical polymerization and grow non-functional polymer chains on the surface of the rubber. Then, the surface was washed with water (by immersion in water at room temperature for five minutes, which was repeated three times), followed by drying.

The vulcanized rubber gasket on which the non-functional polymer chains were formed was immersed in water in an amount 10 times the volume of the vulcanized rubber gasket and subjected to autoclave treatment at 121° C. and 0.2 MPa for two hours twice.

Then, the washed rubber vulcanizate was again immersed in a 3 wt % solution of benzophenone in acetone so that benzophenone was adsorbed onto the surface of the rubber vulcanizate on which non-functional polymer chains were formed, and dried. Next, the surface of the rubber vulcanizate on which non-functional polymer chains were formed was irradiated with LED-UV light having a wavelength of 365 nm for 10 minutes to chemically bond benzophenone to the surface. Thereafter, the surface was washed with acetone to remove unreacted benzophenone. The resulting rubber vulcanizate was taken out and dried.

Next, a fluorine-containing functional monomer solution (Shin-Etsu Chemical Co., Ltd., KY-1203, a mixture of a fluorine-containing epoxy-modified organic silicon compound and a fluorine-containing (meth)acrylic-modified organic silicon compound which are represented by the formulae below) was applied to the surface of the vulcanized rubber gasket where polyacrylic acid was grown. Then, the surface was irradiated with LED-UV light having a wavelength of 365 nm for 15 minutes in an argon gas atmosphere to cause radical polymerization and further grow fluorine-containing functional polymer chains on the polyacrylic acid chains (non-functional polymer chains). In this manner, a surface-modified elastic body (a polymer brush layer on the surface) was obtained.

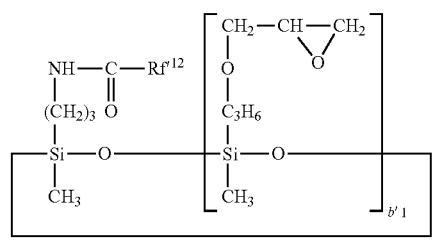

-continued

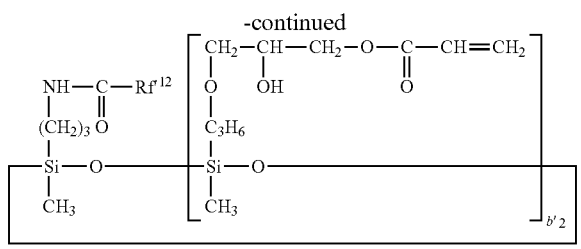

In the formulae, the sum $b'_1+b'_2$ is 2 to 6.5 and $Rf^{12}$ is a group represented by the following formula:

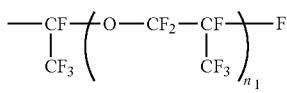

wherein $n_1$ is 2 to 100.

Example 2

A surface-modified elastic body (a polymer brush layer on the surface) was obtained as in Example 1, except that the polymerization time of the fluorine-containing functional monomer solution (irradiation time with LED-UV light) was changed to 30 minutes.

Example 3

A chlorobutyl rubber (degree of unsaturation: 1 to 2%) containing isoprene units was cross-linked by triazine to prepare a vulcanized rubber gasket (vulcanized at 180° C. for 10 minutes), which was then immersed in a 3 wt % solution of benzophenone in acetone so that benzophenone was adsorbed onto the surface of the rubber vulcanizate, followed by drying.

The dried vulcanized rubber gasket was immersed in an aqueous acrylamide solution (2.5 M, 17.8 g of acrylamide dissolved in 100 mL of water) in a glass reaction vessel. Then the gasket was irradiated with LED-UV light having a wavelength of 365 nm for 120 minutes in an argon gas atmosphere to cause radical polymerization and grow non-functional polymer chains on the surface of the rubber. Then, the surface was washed with water (immersing the gasket in water at room temperature for five minutes to wash the gasket was repeated three times) and dried.

The vulcanized rubber gasket on which the non-functional polymer chains were formed was immersed in water in an amount 10 times the volume of the vulcanized rubber gasket and subjected to autoclave treatment at 121° C. and 0.2 MPa for two hours twice.

Then, the washed rubber vulcanizate was again immersed in a 3 wt % solution of benzophenone in acetone so that benzophenone was adsorbed onto the surface of polyacrylamide, and dried. Next, a fluorine-containing functional monomer solution (Shin-Etsu Chemical Co., Ltd., KY-1203) was applied to the surface of the vulcanized rubber gasket where benzophenone was adsorbed onto the surface of polyacrylamide. Then, the surface was irradiated with LED-UV light having a wavelength of 365 nm for 15 minutes in an argon gas atmosphere to cause radical polymerization and further grow fluorine-containing functional polymer chains on the polyacrylamide chains (non-functional polymer chains). In this manner, a surface-modified elastic body (a polymer brush layer on the surface) was obtained.

Example 4

A chlorobutyl rubber (degree of unsaturation: 1 to 2%) containing isoprene units was cross-linked by triazine to prepare a vulcanized rubber gasket (vulcanized at 180° C. for 10 minutes), which was then immersed in a 3 wt % solution of benzophenone in acetone so that benzophenone was adsorbed onto the surface of the rubber vulcanizate, followed by drying.

The dried vulcanized rubber gasket was immersed in a mixed aqueous solution containing acrylic acid and acrylamide at a ratio of 25:75 (2.5 M, 4.5 g of acrylic acid and 13.4 g of acrylamide dissolved in 100 mL of water) in a glass reaction vessel. Then, the gasket was irradiated with LED-UV light having a wavelength of 365 nm for 60 minutes in an argon gas atmosphere to cause radical polymerization and grow non-functional polymer chains on the rubber surface. Then, the surface was washed with water (immersing the gasket in water at room temperature for five minutes to wash the gasket was repeated three times) and dried.

The vulcanized rubber gasket on which the non-functional polymer chains were formed was immersed in water in an amount 10 times the volume of the gasket and subjected to autoclave treatment at 121° C. and 0.2 MPa for two hours twice.

Then, the washed rubber vulcanizate was immersed in a 3 wt % solution of benzophenone in acetone so that benzophenone polyacrylamide, and dried. Next, a fluorine-containing functional monomer solution (Shin-Etsu Chemical Co., Ltd., KY-1203) was applied to the surface of the vulcanized rubber gasket where benzophenone was adsorbed onto the surface of the polyacrylic acid and polyacrylamide. Then, the surface was irradiated with LED-UV light having a wavelength of 365 nm for 15 minutes in an argon gas atmosphere to cause radical polymerization and further grow fluorine-containing functional polymer chains on the polyacrylic acid chains and polyacrylamide chains (non-functional polymer chains). In this manner, a surface-modified elastic body (a polymer brush layer on the surface) was obtained.

Example 5

A chlorobutyl rubber (degree of unsaturation: 1 to 2%) containing isoprene units was cross-linked by triazine to prepare a vulcanized rubber gasket (vulcanized at 180° C. for 10 minutes), which was then immersed in a benzophenone-containing acrylamide aqueous solution (2.5 M, 17.8 g of acrylamide dissolved in 100 mL of water and 2 mg of benzophenone further dissolved therein) in a glass reaction vessel. The rubber surface was irradiated with LED-UV light having a wavelength of 365 nm for 150 minutes in an argon gas atmosphere to cause radical polymerization and grow non-functional polymer chains on the rubber surface. Then, the surface was washed with water (immersing the gasket in water at room temperature for five minutes to wash the gasket was repeated three times) and dried.

The vulcanized rubber gasket on which the non-functional polymer chains were formed was immersed in water in an amount 10 times the volume of the vulcanized rubber gasket and subjected to autoclave treatment at 121° C. and 0.2 MPa for two hours twice.

Next, a fluorine-containing functional monomer solution (Shin-Etsu Chemical Co., Ltd., KY-1203) in which benzophenone monomers was applied to the washed surface of the vulcanized rubber gasket. Then, the surface was irradiated with LED-UV light having a wavelength of 365 nm for 20 minutes in an argon gas atmosphere to cause radical polymerization and further grow fluorine-containing functional polymer chains on the polyacrylamide chains (non-functional polymer chains). In this manner, a surface-modified elastic body (a polymer brush layer on the surface) was obtained.

Example 6

A chlorobutyl rubber (degree of unsaturation: 1 to 2%) containing isoprene units was cross-linked by triazine to prepare a vulcanized rubber gasket (vulcanized at 180° C. for 10 minutes), which was then immersed in a 3 wt % acetone solution of 2,4-diethylthioxane so that 2,4-diethylthioxane was adsorbed on the surface of the rubber vulcanizate, followed by drying.

The dried vulcanized rubber gasket was immersed in an aqueous acrylamide solution (2.5 M, 17.8 g of acrylamide dissolved in 100 mL of water) in a glass reaction vessel. Then the gasket was irradiated with LED-UV light having a wavelength of 365 nm for 70 minutes in an argon gas atmosphere to cause radical polymerization and grow non-functional polymer chains on the surface of the rubber. Then, the surface was washed with water (cycle of immersing the gasket in water at room temperature for five minutes and washing the gasket was repeated three times) and dried.

The vulcanized rubber gasket on which the non-functional polymer chains were formed was immersed in water in an amount 10 times the volume of the gasket and subjected to autoclave treatment at 135° C. and 0.32 MPa for two hours twice.

Then, the washed rubber vulcanizate was immersed in a 3 wt % acetone solution of 2,4-diethylthioxane so that 2,4-diethylthioxane was adsorbed onto the surface of the polyacrylamide and dried. Next, a fluorine-containing functional monomer solution (Shin-Etsu Chemical Co., Ltd., KY-1203) was applied to the surface of the vulcanized rubber gasket where benzophenone was adsorbed onto the surface of the polyacrylamide. Then, the surface was irradiated with LED-UV light having a wavelength of 365 nm for 15 minutes in an argon gas atmosphere to cause radical polymerization and further grow fluorine-containing functional polymer chains on the polyacrylic acid chains and the polyacrylamide chains (non-functional polymer chains). In this manner, a surface-modified elastic body (a polymer brush layer on the surface) was obtained.

Example 7

A chlorobutyl rubber (degree of unsaturation: 1 to 2%) containing isoprene units was cross-linked by triazine to prepare a vulcanized rubber gasket (vulcanized at 180° C. for 10 minutes), which was then immersed in a 3 wt % acetone solution of 2,4-diethylthioxane so that 2,4-diethylthioxane was adsorbed onto the surface of the rubber vulcanizate, followed by drying.

The dried vulcanized rubber gasket was immersed in an aqueous acrylonitrile solution (1.25 M, 8.7 ml of acrylonitrile dissolved in 100 mL of water) in a glass reaction vessel. Then the gasket was irradiated with LED-UV light having a wavelength of 365 nm for 40 minutes in an argon gas atmosphere to cause radical polymerization and grow non-functional polymer chains on the rubber surface. Then, the surface was washed with water (immersing the gasket in water at room temperature for five minutes to wash the gasket was repeated three times) and dried.

The vulcanized rubber gasket on which the non-functional polymer chains were formed was immersed in water in an amount 10 times the volume of the vulcanized rubber gasket and subjected to autoclave treatment at 135° C. and 0.32 MPa for two hours twice.

Then, the washed rubber vulcanizate was immersed in a 3 wt % acetone solution of 2,4-diethylthioxane so that 2,4-diethylthioxane was adsorbed onto the surface of the polyacrylonitrile, and dried. Next, a fluorine-containing functional monomer solution (Shin-Etsu Chemical Co., Ltd., KY-1203) was applied to the surface of the vulcanized rubber gasket where 2,4-diethylthioxane was adsorbed onto the surface of polyacrylonitrile. Then, the surface was irradiated with LED-UV light having a wavelength of 365 nm for 15 minutes in an argon gas atmosphere to cause radical polymerization and further grow fluorine-containing functional polymer chains on the polyacrylonitrile chains (non-functional polymer chains). In this manner, a surface-modified elastic body (a polymer brush layer on the surface) was obtained.

Comparative Example 1

A chlorobutyl rubber (degree of unsaturation: 1 to 2%) containing isoprene units was cross-linked by triazine to prepare a vulcanized rubber gasket (vulcanized at 180° C. for 10 minutes), which was then used as it was.

Comparative Example 2

A surface-modified elastic body (a polymer brush layer on the surface) was obtained as in Example 1, except that the process of immersing the vulcanized rubber gasket in a vessel filled with water and performing autoclave treatment was omitted.

The surface-modified elastic bodies prepared in the examples and comparative examples were evaluated by the methods mentioned below.

(Length of Entire Polymer Chains)

To determine the length of the polymer chains formed on the surface of the rubber vulcanizate, a cross section of the measured with an SEM at an accelerating voltage of 15 kV and a magnification of 1,000 times. The thickness of the polymer layer photographed was determined and used as the length of the polymer chains.

(Friction Resistance)

To determine the friction resistance of the surface of the surface-modified elastic body, the vulcanized rubber gaskets prepared in the examples and comparative examples were each inserted into a COP resin barrel of a syringe and then pushed towards the end of the barrel (push rate: 30 mm/min) using a tensile tester while friction resistance was measured. The friction resistance of the examples was expressed as a friction resistance index relative to the friction resistance of Comparative Example 1 set to 100 based on the equation below. A lower index indicates lower friction resistance.

(Friction resistance index)=(Friction resistance of each example)/(Friction resistance of Comparative Example 1)×100

TABLE 1

|  | Example | | | | Comparative Example | |
|---|---|---|---|---|---|---|
|  | 1 | 2 | 3 | 4 | 1 | 2 |
| Length of entire polymer chain (nm) | 7000 | 8000 | 6000 | 6000 | — | 12000 |
| Non-functional polymer chain:Fluorine-containing functional polymer chain (length) | 70:30 | 60:40 | 65:35 | 65:35 | — | 85:15 |
| Friction resistance index | 1 | 0.9 | 0.9 | 0.8 | 100 | 1.25 |

TABLE 2

|  | Example | | |
|---|---|---|---|
|  | 5 | 6 | 7 |
| Length of entire polymer chain (nm) | 5500 | 6500 | 8000 |
| Non-functional polymer chain:Fluorine-containing functional polymer chain (length) | 65:35 | 65:35 | 65:35 |
| Friction resistance index | 1 | 0.85 | 0.75 |

The results shown in Table 1 and Table 2 demonstrate that, in comparison with Comparative Example 1, the surfaces of the surface-modified elastic bodies of the examples exhibited greatly reduced friction resistances and therefore had good sliding properties.

Moreover, in comparison with Comparative Example 2 in which the process of immersing the vulcanized rubber gasket in water and performing autoclave treatment was omitted, the surfaces of the modified elastic bodies of the examples had better sliding properties, which leads to reduction in the pain inflicted on a patient during injection.

In addition, since only the surface was modified, the sealing properties of these surface-modified elastic bodies were similar to Comparative Example 1.

Thus, when these surface-modified elastic bodies are used as gaskets for syringe plungers, they provide sufficient sealing properties while reducing the friction of the plunger with the syringe barrel, and therefore they enable easy and accurate treatment with syringes. Moreover, since they have a small difference between static and kinetic friction coefficients, the start of pushing the plunger and the subsequent inward movement of the plunger can be smoothly carried out without pulsation. Also, if polymer chains are formed on the inner surface of a syringe barrel made of a thermoplastic elastomer, treatment with the syringe can be readily carried out as described above.

Furthermore, the above-mentioned effects can also be expected when polymer chains are formed on the surfaces of the grooves formed on the tread or of the sidewalls of tires for use on vehicles such as passenger cars, on the surfaces of diaphragms, on the sliding surfaces of skis or snowboards, or on the surfaces of swimsuits, road signs, sign boards, or the like.

REFERENCE SIGNS LIST

1: Gasket
11a, 11b, 11c: Circular protruding portion
13: Bottom surface
2: Tread portion
3a: Longitudinal center groove
3b: Longitudinal shoulder groove
5: Fine groove
6: Beveled intermediate groove
7: Connecting groove
8, 8a, 8b: Lateral shoulder groove

The invention claimed is:

1. A method for surface-modifying a rubber vulcanizate or a thermoplastic elastomer as a modification target, the method comprising:
   step 1 of forming polymerization initiation points A on a surface of the modification target;
   step 2 of radically polymerizing a non-functional monomer starting from the polymerization initiation points A to grow non-functional polymer chains;
   step 3 of washing the modification target on which the non-functional polymer chains are grown;
   step 4 of forming polymerization initiation points B on a surface of the non-functional polymer chains; and
   step 5 of radically polymerizing a fluorine-containing functional monomer starting from the polymerization initiation points B to grow fluorine-containing functional polymer chains,
   the washing being carried out with at least one selected from the group consisting of hot water at a temperature of 50° C. to 150° C., steam, and an organic solvent,
   the non-functional monomer being at least one selected from the group consisting of acrylic acid, acrylic acid esters, alkali metal salts of acrylic acid, amine salts of acrylic acid, acrylamide, dimethylacrylamide, diethylacrylamide, isopropylacrylamide, hydroxyethylacrylamide, methoxymethylacrylamide, acryloylmorpholine, methoxyethyl acrylate, hydroxyethyl acrylate, methacrylic acid, methacrylic acid esters, alkali metal salts of methacrylic acid, amine salts of methacrylic acid, methacrylamide, dimethylmethacrylamide, diethylmethacrylamide, isopropylmethacrylamide, hydroxyethylmethacrylamide, methacryloylmorpholine, methoxyethyl methacrylate, hydroxyethyl methacrylate, and acrylonitrile,
   the fluorine-containing functional monomer being an acrylate or methacrylate containing at least one of the following groups: a fluoroalkyl group, a fluoroalkylether group, and a dimethylsiloxane group.

2. The method according to claim 1,
   wherein the step 2 comprises radically polymerizing a non-functional monomer starting from the polymerization initiation points A by irradiation with LED light having a wavelength of 300 to 450 nm to grow non-functional polymer chains, and
   the step 5 comprises radically polymerizing a fluorine-containing functional monomer starting from the polymerization initiation points B by irradiation with LED light having a wavelength of 300 to 450 nm to grow fluorine-containing functional polymer chains.

3. The method according to claim 1,
   wherein the step 1 comprises adsorbing a photopolymerization initiator A onto a surface of the modification target, optionally followed by irradiation with LED light having a wavelength of 300 to 400 nm, to form polymerization initiation points A from the photopolymerization initiator A on the surface, and the step 4 comprises adsorbing a photopolymerization initiator B onto a surface of the non-functional polymer chains, optionally followed by irradiation with LED light having a wavelength of 300 to 400 nm, to form polymerization initiation points B from the photopolymerization initiator B on the surface.

4. A method for surface-modifying a rubber vulcanizate or a thermoplastic elastomer as a modification target, the method comprising:
step I of radically polymerizing a non-functional monomer in the presence of a photopolymerization initiator A on a surface of the modification target to grow non-functional polymer chains;
step II of washing the modification target on which the non-functional polymer chains are grown; and
step III of radically polymerizing a fluorine-containing functional monomer in the presence of a photopolymerization initiator B on a surface of the non-functional polymer chains to grow fluorine-containing functional polymer chains,
the washing being carried out with at least one selected from the group consisting of hot water at a temperature of 50° C. to 150° C., steam, and an organic solvent,
the non-functional monomer being at least one selected from the group consisting of acrylic acid, acrylic acid esters, alkali metal salts of acrylic acid, amine salts of acrylic acid, acrylamide, dimethylacrylamide, diethylacrylamide, isopropylacrylamide, hydroxyethylacrylamide, methoxymethylacrylamide, acryloylmorpholine, methoxyethyl acrylate, hydroxyethyl acrylate, methacrylic acid, methacrylic acid esters, alkali metal salts of methacrylic acid, amine salts of methacrylic acid, methacrylamide, dimethylmethacrylamide, diethylmethacrylamide, isopropylmethacrylamide, hydroxyethylmethacrylamide, methacryloylmorpholine, methoxyethyl methacrylate, hydroxyethyl methacrylate, and acrylonitrile,
the fluorine-containing functional monomer being an acrylate or methacrylate containing at least one of the following groups: a fluoroalkyl group, a fluoroalkylether group, and a dimethylsiloxane group.

5. The method according to claim 3,
wherein the photopolymerization initiator is at least one of a benzophenone compound or a thioxanthone compound.

6. The method according to claim 1,
wherein the rubber vulcanizate or thermoplastic elastomer contains an allylic carbon atom which is adjacent to a double bond.

7. The method according to claim 1,
wherein the polymerization is carried out in an inert gas atmosphere.

8. The method according to claim 1,
wherein the polymerization is carried out under evacuation.

9. The method according to claim 1,
wherein the fluorine-containing functional monomer is a fluorine-containing (meth)acrylic-modified organic silicon compound obtained by addition reaction of a fluorine-containing epoxy-modified organic silicon compound (A) represented by the following formula (1) with an unsaturated monocarboxylic acid (B) containing a (meth)acrylic group:

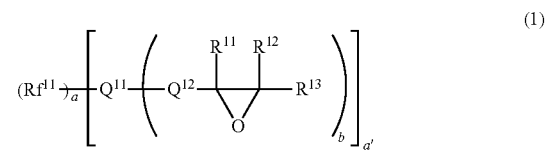

wherein $Rf^{11}$ is a monovalent or bivalent group having a fluoroalkyl or fluoropolyether structure with a molecular weight of 100 to 40,000; $Q^{11}$ is a (a+b)-valent linking group that contains at least a+b silicon atoms and has a siloxane structure, a non-substituted or halogen-substituted silalkylene structure, a silarylene structure, or a combination of two or more of these structures, and optionally has a cyclic structure; $Q^{12}$ is a bivalent C1-C20 hydrocarbon group optionally having a cyclic structure and optionally interrupted by an ether bond or ester bond; $R^{11}$ to $R^{13}$ are each independently a hydrogen atom or a monovalent C1-C10 hydrocarbon group, the hydrogen atoms of $R^{11}$ to $R^{13}$ may be partially or entirely substituted with halogen atoms, and $R^{11}$ and $R^{12}$ may be joined to form a ring together with the carbon atoms to which $R^{11}$ and $R^{12}$ are attached; when $Rf^{11}$ is monovalent, a' is 1 and a is an integer of 1 to 6, and when $Rf^{11}$ is bivalent, a is 1 and a' is 2; and b is an integer of 1 to 20.

10. The method according to claim 9,
wherein $Rf^{11}$ in the formula (1) contains 1 to 500 repeating units represented by the following formula:

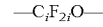

wherein i in each unit is independently an integer of 1 to 6.

11. The method according to claim 9,
wherein $Q^{11}$ in the formula (1) is represented by either of the following formulae:

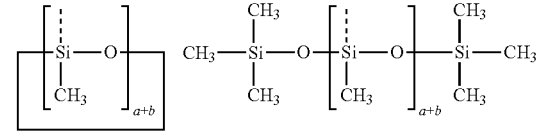

wherein a and b are defined as above, a units and b units are each arranged at random, and the bond indicated by the dashed line in each of a units and b units is attached to $Rf^{11}$ or the group represented by the following formula:

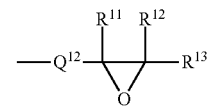

wherein $Q^{12}$ and $R^{11}$ to $R^{13}$ are as defined in the formula (1).

12. The method according to claim 9,
wherein $Rf^{11}$ in the formula (1) is represented by the following formula (3):

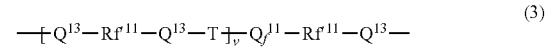

wherein $Rf^{11}$ is a bivalent perfluoropolyether group having a molecular weight of 300 to 30,000 and optionally internally branched; $Q^{13}$ is a bivalent organic group optionally containing an oxygen, nitrogen, fluorine, or silicon atom, and optionally having a cyclic structure or an unsaturated bond; $Q_f^{11}$ is $Q^{13}$ or a fluorine atom; T is a linking group represented by the following formula (4):

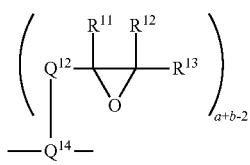

wherein $R^{11}$ to $R^{13}$, $Q^{12}$, a, and b are as defined in the formula (1), and $Q^{14}$ is a (a+b)-valent linking group that contains at least a+b silicon atoms and has a siloxane structure, a non-substituted or halogen-substituted silalkylene structure, a silarylene structure, or a combination of two or more of these structures; and v is an integer of 0 to 5, and when $Q_f^{11}$ is a fluorine atom, v is 0.

13. The method according to claim 1,
wherein the fluorine-containing functional monomer is a mixture of a fluorine-containing epoxy-modified organic silicon compound represented by the following formula and a fluorine-containing (meth)acrylic-modified organic silicon compound represented by the following formula:

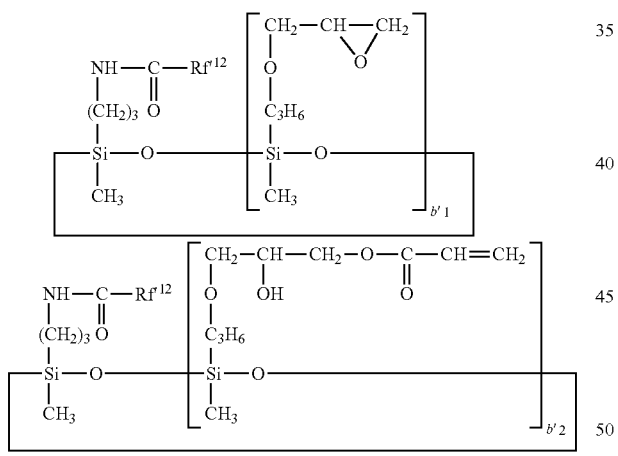

wherein the sum $b'_1+b'_2$ is 2 to 6.5 and $R_f^{'12}$ is a group represented by the following formula:

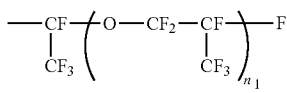

wherein $n_1$ is 2 to 100.

14. The method according to claim 1,
wherein the fluorine-containing functional monomer is a polyfunctional (meth)acrylate compound comprising a cyclic siloxane represented by the following formula:

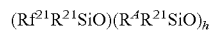

$$(Rf^{21}R^{21}SiO)(R^4R^{21}SiO)_h$$

wherein $R^{21}$ is a hydrogen atom, a methyl group, an ethyl group, a propyl group, or a phenyl group; $Rf^{21}$ is a fluorine-containing organic group; $R^4$ is a (meth)acrylic group-containing organic group; and h≥2,
the polyfunctional (meth)acrylate compound containing three or more F atoms and three or more Si atoms per molecule.

15. The method according to claim 14,
wherein $R^4$ is attached to the Si atom via a Si—O—C bond.

16. The method according to claim 14,
wherein $Rf^{21}$ is a group represented by $C_tF_{2t+1}(CH_2)_u$— wherein t is an integer of 1 to 8 and u is an integer of 2 to 10, or a perfluoropolyether-substituted alkyl group.

17. The method according to claim 1,
wherein the fluorine-containing functional monomer has an infrared absorption spectrum comprising strong absorption peaks at around 1045 $cm^{-1}$ and around 1180 $cm^{-1}$, absorption peaks at around 806 $cm^{-1}$ and around 1720 $cm^{-1}$, a weak absorption peak at around 1532 $cm^{-1}$, and a broad and weak absorption peak at around 3350 $cm^{-1}$.

18. The method according to claim 1,
wherein the fluorine-containing functional monomer has a $^{13}C$ NMR spectrum in chloroform-d solution comprising signals at chemical shifts of about 13.01, 14.63, 23.04, 40.13, 50.65, 63.54, 68.97, 73.76, 76.74, 77.06, 77.38, 113.21, 114.11, 116.96, 117.72, 118.47, 128.06, 131.38, 156.46, and 166.02 ppm.

19. The method according to claim 1,
wherein the fluorine-containing functional monomer has a $^1H$ NMR spectrum in chloroform-d solution comprising signals at chemical shifts of about 3.40, 3.41, 3.49, 3.60, 5.26, 5.58, 6.12, 6.14, 6.40, 6.42, and 6.46 ppm.

20. The method according to claim 1,
wherein a solution of the non-functional monomer or fluorine-containing functional monomer, or the non-functional monomer or fluorine-containing functional monomer in the liquid state contains a polymerization inhibitor, and is polymerized in the presence of the polymerization inhibitor.

21. The method according to claim 20,
wherein the polymerization inhibitor is 4-methylphenol.

22. The method according to claim 1,
wherein a length of the entire polymer chain, including the non-functional polymer chain and the fluorine-containing functional polymer chain, is 10 to 50000 nm.

23. The method according to claim 1,
wherein a ratio in length between the non-functional polymer chain and the fluorine-containing functional polymer chain is 50:50 to 99.9:0.1.

* * * * *